(12) United States Patent
Varki et al.

(10) Patent No.: US 6,596,705 B1
(45) Date of Patent: Jul. 22, 2003

(54) INHIBITION OF L-SELECTIN AND P-SELECTION MEDIATED BINDING USING HEPARIN

(75) Inventors: Ajit Varki, Del Mar, CA (US); Andrea Koenig, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/246,993

(22) Filed: Feb. 8, 1999

Related U.S. Application Data
(60) Provisional application No. 60/073,998, filed on Feb. 19, 1998.

(51) Int. Cl.[7] ............................................ A61K 31/727
(52) U.S. Cl. ......................................................... 514/56
(58) Field of Search ........................................... 514/56

(56) References Cited

U.S. PATENT DOCUMENTS

| | | | |
|---|---|---|---|
| 5,464,815 A | 11/1995 | Chamow et al. ................ | 514/8 |
| 5,527,785 A | 6/1996 | Bevilacqua et al. ........... | 514/56 |
| 5,777,081 A | 7/1998 | Michalski et al. ........... | 530/380 |
| 6,153,211 A | * 11/2000 | Hubbell et al. .............. | 424/426 |

FOREIGN PATENT DOCUMENTS

| | | |
|---|---|---|
| CA | 2105528 | 9/1993 |
| WO | 92/02232 | 2/1992 |

OTHER PUBLICATIONS

Sigma Chemical Company Catalog "Biochemicals, Organic Compounds for Research, and Diagnostic Reagents" 1995.*
Dagenais et al. *FASEB J.* Feb. 28, 1997, 11 (3), A311, Abstract No. 1805.*
Borsig et al. (2001) "Heparin and cancer revisited: Mechanistic connections involving platelets, P–selectin, carcinoma mucins, and tumor metastasis," Proc. Natl. Acad. Sci. USA 58:3352–3357.
Hubeau et al. (2001) "Quantitative analysis of inflammatory cells infiltrating the cystic fibrosis airway mucosa," Clin. Exp. Immunol. 124(1):69–76.
De Rose et al. (1998) "Circulating adhesion molecules in cystic fibrosis,", Am. J. Respir. Crit. Care Med. 157:1234–1239.
Scanlin et al. (1999) "Terminal glycosylation in cystic fibrosis," Biochim Biophys. Acta 1455:241–253.
Russell et al. (1998) "Neutrophil adhesion molecule surface expression and responsiveness in cystic fibrosis," Am. J. Respir. Crit. Care Med. 157:756–761.
Kishimoto et al. (1989) "Neurtrophil Mac–1 and MEL–14 Adhesion Proteins Inversely Regulated by Chemotactic Factors, "Science 245:1238.
Feehan et al. (1996) "Shedding of the Lymphocyte L–Selectin Adhesion Molecule is Inhibited by a Hydroxamic Acid–based Protease Inhibitor," J. Biol. Chem. 271:7019–7024.
Ahmed et al. (1993) "Preventing Bronchoconstriction in Exercise–Induced Asthma with Inhaled Heparin," The New England J. Med. 329:90–95.
Norgard–Sumnicht & Varki, "Endothelial heparan sulfate proteoglycans that bind to L–selection have glucosamine residues with unsubstituted amino groups" *J. Of Bio. Chem.* 270(20): 12012–12024 (May 1995).

* cited by examiner

*Primary Examiner*—Kathleen K. Fonda
(74) *Attorney, Agent, or Firm*—Medlen & Carroll, LLP

(57) ABSTRACT

The present invention provides methods of inhibiting L-selectin and P-selectin mediated binding in a subject by administering heparin to the subject in an amount that does not produce substantial anticoagulant activity or undesirable bleeding in the subject. In addition, the invention provides methods of treating a subject having a pathology characterized, at least in part, by abnormal L-selectin or P-selectin mediated binding by administering heparin to the subject in an amount that results in attaining a concentration of less than about 0.2–0.4 units heparin per ml of plasma in the subject.

26 Claims, 9 Drawing Sheets

INHIBITION OF L-SELECTIN AND P-SELECTION MEDIATED BINDING USING HEPARIN

This application is based on, and claims the benefit of, U.S. Provisional Application No. 60/073,998, filed Feb. 9, 1998, and is incorporated herein by reference.

Each of the references cited herein, including the references numbered 18, 25 and 57 to 200, is incorporated herein by reference.

This invention was made with government support under grant numbers CA38701 and HL23584 awarded by the National Institutes of Health. The government has certain rights in the invention.

BACKGROUND OF THE INVENTION

1. Field of the Invention

The present invention relates generally to molecular biology and, more specifically, to methods of modulating L-selectin and P-selectin mediated binding in a subject by administering heparin to the subject in an amount that does not produce substantial anticoagulation activity or undesirable bleeding.

2. Background Information

L-selectin, E-selectin and P-selectin mediate the initial adhesive events directing the homing of lymphocytes into lymphoid organs, as well as the interactions of leukocytes and other inflammatory cells with endothelium at sites of inflammation. L-selectin is expressed on leukocytes, E-selectin is expressed on endothelium and P-selectin is expressed on platelets and endothelium. The three selectins bind to specific carbohydrate structures on opposing cells, for example, L-selectin binds to platelets and endothelium, whereas P-selectin and E-selectin bind to leukocytes.

Selectin adhesion is involved in disorders such as pathologic reperfusion injury, inflammatory disorders and autoimmune disorders. Selectin interactions also can mediate primary adhesive mechanisms involved in the metastasis of certain epithelial cancers. Thus, selectins are potential therapeutic targets for the treatment of pathologies characterized by undesirable or abnormal interactions mediated by selecting.

Much work has been directed to finding small carbohydrate molecules for use as competitive inhibitors to block selectin mediated interactions. For example, the tetrasaccharide sialyl-Lewis$^x$ (SLe$^x$) is recognized by all three selectins, and is a component of many naturally occurring high affinity selectin ligands, for example, the myeloid cell ligand for P-selectin, called PSGL-1. However, the interaction of selectins with purified SLe$^x$ is weak and SLe$^x$ demonstrates little selectivity among the selecting. Thus, while SLe$^x$ and related structures may provide some therapeutic use, they are limited in being weak and nonselective inhibitors of selectin binding. Furthermore, they are very expensive to produce in the quantities required for treatment.

Heparan sulfates (HS) are naturally occurring glycosaminoglycan (GAG) chains that have diverse biological functions, generally mediated by their ability to interact with growth factors, receptors and the like. Heparin, which is a heavily modified GAG, is a heterogeneous mixture of long, unbranched carbohydrate chains consisting of repeating disaccharide units composed of uronic acids alternating with glucosamine residues which can be extensively modified.

Due to its anticoagulant activity, heparin is used clinically as an antithrombotic agent for treating human subjects having a disorder resulting from the abnormal or undesirable activation of the blood clotting cascade. Heparin's anticoagulant activity is the result of a modified pentasaccharide sequence that is present on certain heparin chains and binds to antithrombin III, a regulatory protein of the clotting cascade. Heparin chains that are longer than about 18 saccharide units and that have the modified pentasaccharide sequence can enhance the ability of antithrombin III to bind to and inhibit the function of coagulation factors, thereby inhibiting the blood clotting cascade. Pharmaceutical preparations of heparin are enriched for antithrombin III binding chains, but also contain a mixture of other components.

L-selectin and P-selectin interact with a variety of sulfated compounds including heparan sulfates, porcine intestinal mucosal (PIM) heparin and its fragments. Although L-selectin and P-selectin similarly bind to HS chains and PIM-heparin, they are different from E-selectin, which fails to bind the HS chains or PIM-heparin. The observation that L-selectin binding to endothelial cell HS chains is calcium dependent indicates that this interaction is similar to selectin's interaction with natural ligands. This suggestion is supported by the ability of small heparin fragments to compete with L-selectin and P-selectin binding to SLe$^x$.

Pharmaceutical preparations of heparin are similar to crude commercial PIM-heparin. Thus, it might be expected that pharmaceutical heparin would have been used for inhibiting the binding of L-selectin and P-selectin to ligands present on cells in humans. However, heparin has not been used for the purpose of inhibiting L-selectin and P-selectin binding in humans because of concerns about potential undesirable side effects associated with its anticoagulant activity.

To address the problem of undesirable anticoagulant activity, low molecular weight (LMW) oligosaccharides, which are derived from heparin, but lack anticoagulant activity, have been prepared. When injected into mice, such LMW heparins can inhibit inflammation by binding to L-selectin and P-selectin. However, the cost of preparing LMW forms of heparin combined with the cost of new product testing to obtain FDA approval for use in humans is often prohibitive. In addition, it is unclear how efficacious the LMW heparins would be in inhibiting L-selectin and P-selectin binding when administered to a human subject. Thus, a need exists for developing methods of using readily available pharmaceutical compositions to inhibit L-selectin and P-selectin mediated binding in a subject without producing undesirable side effects. The present invention satisfies this need and provides related advantages as well.

SUMMARY OF THE INVENTION

The present invention provides a method of inhibiting L-selectin and P-selectin binding in a subject by administering to the subject an amount of heparin that does not produce substantial anticoagulant activity or undesirable bleeding. Thus, the invention provides methods of administering heparin in amounts that result in attaining a concentration less than about 0.2–0.4 units heparin per ml of plasma in the subject, such levels which inhibit L-selectin or P-selectin mediated binding in the subject. The invention further provides methods of treating a subject having an L-selectin or P-selectin related pathology by administering heparin in an amount that does not produce substantial anticoagulant activity or undesirable bleeding, for example, an amount that results in a concentration less than about 0.2–0.4 units heparin per ml of plasma in the subject.

BRIEF DESCRIPTION OF THE DRAWINGS

FIG. 6A shows the results for octasaccharides, while FIG. 6B shows the results for decasaccharides, FIG. 6C shows the results for dodecasaccharides, and FIG. 6D shows the results for tetrasaccharides. In these experiments, the columns were eluted with 2 mM EDTA ("2"), followed by 20 mM EDTA ("20) buffer. Arrows as in FIG. 1.

FIG. 7A shows the results for tetradecasaccharides that originally were unbound (Pool A), while FIG. 7B shows the results for tetradecasaccharides that were slightly retarded (Pool B), FIG. 7C shows the results for tetradecasaccharides that were retarded (Pool C), and FIG. 7D shows the results for tetradecasaccharides that were eluted with EDTA. The tetradecasaccharides from each pool were eluted with 2 mM EDTA buffer. The horizontal bar above each chromatogram indicates where the pool originally eluted from the column. Arrows as in FIG. 1.

FIG. 8A shows the inhibitory properties of a pharmaceutical heparin preparation (unfractionated; closed triangles) or LMW heparins (LOVENOX, open squares; FRAGMIN, closed circles) on the binding of L-selectin to immobilized SLe* using ELISA inhibition experiments, while

DETAILED DESCRIPTION OF THE INVENTION

Figure 1A:
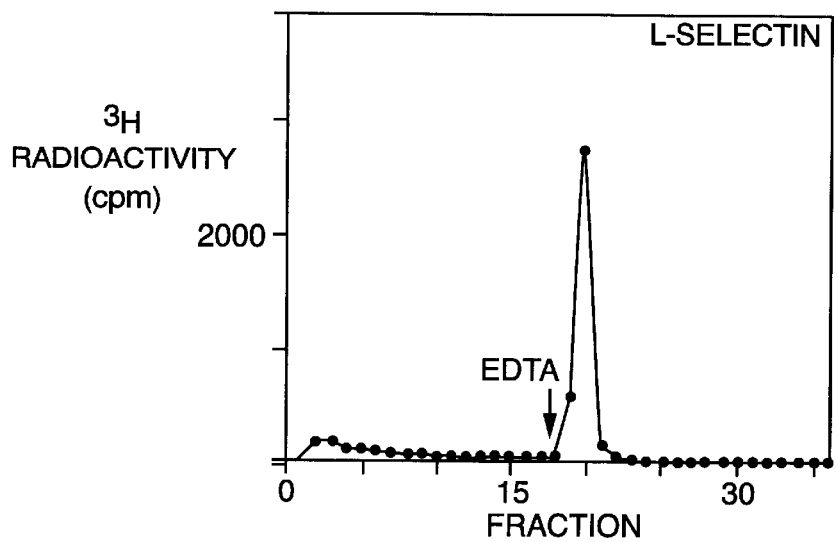
FIG. 1A shows that heparin sulfate obtained from endothelial cells binds to L-selectin.

The present invention provides methods of inhibiting L-selectin or P-selectin mediated binding in a subject by administering to the subject an amount of heparin that does not produce substantial anticoagulant activity or undesirable bleeding in the subject. Heparin is used clinically as an anticoagulant to reduce blood clotting in an individual. Heparin has a narrow therapeutic window and is administered to individuals for anticoagulant therapy in an amount sufficient to achieve levels of 0.2–0.4 units per ml of plasma (Ginsberg, *New Engl. J. Med.* 335:1816–1828 (1996)). Individuals administered heparin at concentrations less than 0.2 units per ml of plasma are significantly more likely to exhibit a recurrence of thrombosis, indicating that administration of an amount of heparin that results in a concentration of less than about 0.2 units per ml of plasma generally is not optimal for anticoagulant therapy of an active thrombus.

As disclosed herein, heparin, as formulated for clinical use, can inhibit the binding of P-selectin and L-selectin to their ligands. Significantly, approximately one-fifth to one-tenth of the amount of pharmaceutical heparin that is needed for anticoagulant therapy in humans effectively inhibits L-selectin and P-selectin mediated binding. Thus, the invention provides a means to inhibit L-selectin and P-selectin mediated binding in a subject by administering heparin in an amount that does not produce substantial anticoagulant activity or undesirable bleeding in the subject.

The amount of heparin administered to a subject to inhibit L-selectin or P-selectin binding is characterized in that it does not produce undesirable bleeding as a side effect, although it can produce mild anticoagulant activity. As a result, side effects such as bleeding complications that are associated with using heparin for anticoagulant therapy are not a concern. The amount of heparin administered in a method of the invention results in a concentration of less than about 0.2 to 0.4 units heparin/ml plasma, generally about 0.1 to 0.2 units heparin/ml plasma, or about 0.05 to 0.1 units heparin/ml plasma, and can be about 0.02 units heparin/ml plasma or less.

The invention additionally provides a method of inhibiting P-selectin mediated binding, but not L-selectin mediated binding, in a subject by administering heparin in an amount that results in a concentration of about 0.02 to 0.05 units heparin/ml plasma, preferably about 0.005 to 0.02 units heparin/ml plasma to the subject. For example, an amount of heparin that results in about 0.002 units heparin/ml plasma can be administered to a subject to inhibit P-selectin mediated binding, whereas such a concentration of heparin does not substantially inhibit L-selectin mediated binding.

Although the ability of heparin to inhibit L-selectin and P-selectin binding has been established, its anticoagulant activity has prevented clinicians from using heparin to inhibit L-selectin and P-selectin binding in a subject (Yednock et al., *J. Cell Biol.* 104:713–723 (1987); Skinner et al., *Biochem. Biophys. Res. Commun.* 164:1373–1379 (1989); Aruffo et al., *Cell* 67:35–44 (1991); Handa et al., *Biochem. Biophys. Res. Commun.* 181:1223–1230 (1991); Skinner et al., *J. Biol. Chem.* 266:5371–5374 (1991); Needham and Schnaar, *Proc. Natl. Acad. Sci. USA* 90:1359–1363 (1993); Nelson et al., *Blood* 82:3253–3258 (1993); Yuen, et al., *J. Biol. Chem.* 269:1595–1598 (1994); Mitsuoka et al., *Biochem. Biophys. Res. Commun.* 230:546–551 (1997); Yoshino et al., *J. Med. Chem.* 40:455–462 (1997); Norgard-Sumnicht et al., *Science* 261:480–483 (1993)). Thus, molecules that can inhibit L-selectin and P-selectin binding without exhibiting anticoagulant activity have been identified. For example, Bevilacqua et al. demonstrated that particular low molecular weight fractions of heparin which lack anticoagulant activity modulate selectin binding (U.S. Pat. No. 5,527,785, issued Jun. 18, 1996, which is incorporated herein by reference). Bevilacqua et al. also used crude nonpharmaceutical grade heparin to inhibit selectin binding in vitro. However, Bevilacqua et al. stated that heparin compositions that contain the pentasaccharide antithrombin III binding sequence, which is present in pharmaceutical heparin preparations, should not be used for inhibiting selectin mediated binding in a subject due to its anticoagulant activity.

As disclosed herein, pharmaceutical preparations of heparin inhibit L-selectin and P-selectin mediated binding at concentrations less than about 0.2–0.4 units heparin per ml of plasma. This amount of heparin can produce mild anticoagulant activity in humans, but usually does not produce undesirable bleeding. For example, two separate lots of unfractionated pharmaceutical heparin significantly inhibited L-selectin and P-selectin binding at concentrations less than the recommended therapeutic levels targeted for anticoagulation therapy in a subject. In particular, the concentration of pharmaceutical heparin needed to inhibit 50% of the binding ($IC_{50}$) of $SLe^x$ to L-selectin and P-selectin was 0.07–0.08 units/ml and 0.01–0.02 units/ml, respectively (see Table 5, below). In addition, $IC_{50}$ values for pharmaceutical heparin to inhibit attachment of HL-60 cells, which express the natural selectin ligand PSGL-1, to immobilized selectins were 0.02–0.03 units/ml for L-selectin and 0.003–0.01 units/ml for P-selectin (Table 5). Thus, clinically approved heparin compositions can inhibit L-selectin and P-selectin mediated binding in an amount that does not produce substantial anticoagulant activity or undesirable bleeding in a subject.

The methods of the invention are useful in treating a subject having an L-selectin or P-selectin related pathology. Many pathological processes involve L-selectin and P-selectin (Table 1) and, as disclosed herein, can be treated by administering heparin in an amount that results in a concentration of less than about 0.2–0.4 units/ml of plasma in a subject. Ischemia and reperfusion, for example, which cause significant tissue injury in clinical disorders such as stroke, myocardial infarction, organ transplantation and organ hypoperfusion, involve L-selectin and P-selectin related processes (Seekamp et al., *Am. J. Pathol.* 144:592–598 (1994); Garcia-Criado et al., *J. Am. Coll. Surgeons* 181:327–334 (1995); Moore et al., *J. Appl. Physiol.* 78:2245–2252 (1995); Mihelcic et al., *Blood* 84:2322–2328 (1994); Han et al., *J. Immunol.* 155:4011–4015; Rabb et al., *Am. J. Physiol. Renal Fluid Electrolyte Physiol.* 271:F408–F413 (1996); Buerke et al., *J. Clin. Invest.* 93:1140–1148 (1994); Miura et al., *Ann. Thorac. Sura.* 62:1295–1300 (1996); Flynn et al., *Am. J. Physiol. Heart Circ. Physiol.* 271:H2086–H2096 (1996); Ma et al., *Circulation* 88:649–658 (1993); Buerke et al., *J. Pharmacol. Exp. Ther.* 271:134–142 (1994); Lefer, *Ann. Thorac. Surg.* 60:773–777 (1995); Haught et al., *Am. Heart J.* 132:1–8 (1996); Turunen et al., *J. Exp. Med.* 182:1133–1141 (1995); Morikawa et al., *Stroke* 27:951–955 (1996); Weiser et al., *Shock.* 5:402–407 (1996); Yamada et al., *Blood* 86:3487–3492 (1995); Kubes et al., *Am. J. Physiol. Heart Circ. Physiol.* 267:H931–H937 (1994); Gibbs et al., *Surgery* 119:652–656 (1996); Takada et al., *J. Clin. Invest.* 99:2682–2690 (1997); Zizzi et al.,

TABLE 1

| TISSUE | PATHOLOGY | REFERENCE |
|---|---|---|
| Pathological processes involving L-selectin | | |
| Lung | Homing of eosinophils to asthmatic lungs | (58, 59) |
| | Acute lung injury | (60, 61, 61–64) |
| | Inflammation | (65, 66) |
| | Ischemia-reperfusion injury | (67, 68) |
| | Sepsis-induced lung injury | (69) |
| | Adult respitory distress syndrome (ARDS) | (57) |
| Multi- | Inflammatory injury | (70, 70–72) |
| system | Ischemia-reperfusion injury | (67) |
| Immune | HIV infection | (73) |
| | Impaired primary T-cell response | (74) |
| | Common variable immunodefiency (CVID) | (75) |
| | Chronic myelocytic leukemia | (76) |
| | Primary Sjogren's syndrome | (77) |
| | Inflamed extralymphoid tissues | (78) |
| | Humoral immune response (in spleen) | (79) |
| | Meningeal leukemia | (80) |
| Pancreas | Nonobese diabetes | (81–83) |
| Skeletal; | Rheumatoid arthritis | (84) |
| Connective | Anklosing spondylitis | (85) |
| tissue | System sclerosis | (85) |
| | Vasculitis | (85) |
| Muscular | Ischemia-reperfusion injury | (67) |
| Liver | Primary infection with *Listeria monocytogenes* | (86) |
| | Liver inflammation | (87) |

TABLE 1-continued

| TISSUE | PATHOLOGY | REFERENCE |
|---|---|---|
| Skin | Cutaneous inflammation | (88) |
| | Ischemia-reperfusion injury | (89, 90) |
| | Systemic inflammatory response syndrome (SIRS) | (91, 92) |
| Gut | Inflammatory injury | (93) |
| | inflamed peritoneum | (94) |
| | Colon carcinoma | (95) |
| Kidney | Allograph rejection | (25) |
| | Impaired granulocyte function in patients with chronic hemodialysis | (96) |
| | Renal ischemia-reperfusion injury | (97) |
| Circulatory | Inflamed/injured venular endothelium | (98, 99) |
| | Ischemia-reperfusion injury | (100–106) |
| | PMN leukocyte-induced vasocontraction and endothelial dysfuntions | (107) |
| | Hemorrhagic shock injury | (108) |
| | Peripheral arterial disease | (109) |
| | Cardiac transplant rejection | (110) |
| | Activated endothelium | (111) |
| CNS | Pleocytosis in bacterial meningitis | (112) |
| | Allergic encephalomyelitis | (113) |
| | Memogoencephalitis | (114) |
| | Ischemia reperfusion injury | (113) |
| | Multiple sclerosis (MS) | (116) |
| Misc. | Failure of tumor immunity | (117) |
| | Plasmodium falciparium malaria | (118) |
| | Increased soluble L-selectin in premature infants | (119, 120) |
| | Burn injury | (57) |
| | Hyperthyroidism | (121) |
| | Pathological processes involving P-selectin | |
| Lung | Acute lung injury | (60, 63, 64, 22–127) |
| | Reduction of allergic airway hyperresponsiveness | (128) |
| | Ischemia-reperfusion injury | (67) |
| | Inflammation induced by *Streptococcus pneumonia* | (66) |
| | Hyperoxic lung injury | (129) |
| | Small cell lung carcinoma | (130) |
| | Adult respitory distress syndrome (ARDS) | (57) |
| | Asthma | (131) |
| | Pleurisy | (132) |
| Multi-system | Inflammatory injury | (18, 72, 133) |
| | Sepsis and organ failure due to severe trauma | (134) |
| | Burn injury | (57, 135) |
| | Ischemia-reperfusion injury | (67) |
| Immune | Leukocyte adhesion syndrome, type II (LAD II) | (136) |
| | Infection susceptibility | (137) |
| | Primary Sjogren's Syndrome | (77) |
| | Arthus reaction | (138) |
| | Lack of recruitment of Helper T-1 cells to inflammatory sites | (139, 140) |
| | Peripherial neutrophilia | (141) |
| | Altered serum selectin levels in leukemia patients | (142) |
| | Altered hematopoiesis and infection susceptibility | (137, 143) |
| | Severe trauma, sepsis, organ failure | (134) |
| Pancreas | Nonobese diabetes | (144) |
| Skeletal; Connective tissue | Rheumatoid arthritis | (84, 145, 146) |
| Muscular | Skeletal muscle ischemia-reperfusion injury | (147) |
| | Injury and inflammation to striated muscle | (148) |
| Liver | Ischemia-reperfusion injury | (149) |
| | Improved liver function after hemorrhagic shock | (150) |
| Skin | Cutaneous inflammation | (88, 148, 151) |
| | Ear reperfusion injury | (90, 152) |
| | Ischemia-reperfusion injury in dorsal skin | (153) |
| | Delayed-type contact hypersensitivity (DTH) | (92, 154) |
| | Wound Repair | (155) |
| Gut | Intestinal mucosal injury | (156, 157) |
| | Inflammatory injury | (158) |
| | Early phase histamine-induced inflammation | (159) |
| | Ischemia-reperfusion injury | (160) |
| | Inflamed peritoneum | (94) |
| | Intestinal ischemia-reperfusion injury | (161) |
| | Inflammatory bowel disease | (162) |
| | Acute injury to peritoneum | (163) |
| | Abdominal inflammation | (164) |
| | Colon carcinoma | (95, 165) |
| | Intestinal inflammation | (166) |

TABLE 1-continued

| TISSUE | PATHOLOGY | REFERENCE |
| --- | --- | --- |
| Kidney | Neutrophil-dependent glomerular injury | (167) |
| | Acute passive antiglomerular basement membrane nephritis | (114) |
| | Glomerulonephritis | (168) |
| | Ischemia-reperfusion injury | (169, 170) |
| Circulatory | Inflamed/injured venular endothelium | (171) |
| | Splanchnic ischemia-reperfusion injury | (172, 173) |
| | Myocardial ischemia-reperfusion injury | (100–102, 105, 174, 174–178, 178, 179) |
| | PMN leukocyte-induced vasocontraction and endothelial dysfunctions | (107) |
| | Severe vascular trauma | (180) |
| | Atherogenesis brought on by oxidized LDL | (181) |
| | Inflammation and thrombosis | (182) |
| | Hemorrhagic shock injury | (183) |
| | Reduced thrombis formation | (184, 185) |
| | Atherosclerotic vascular disease | (186) |
| | Disrupted blood hemostasis | (187) |
| | Increased infection susceptibility | (143) |
| | Altered hematopoiesis | (143) |
| | Grey platelet syndrome | (188) |
| | Peripherial arterial disease | (109) |
| | Endothelial cell hypoxia and hypoxia regeneration | (189, 190) |
| | Enhanced heart allograft afteriosclerosis | (191) |
| | Hypercholesterolemia | (192) |
| | Angina pectoris/Unstable angina | (193, 194) |
| | Coronary spasm | (195) |
| | Vasocontraction and endothelial cell dysfunction | (107) |
| | Atherogenesis and hypertension | (186) |
| CNS | Ischemia-reperfusion injury | (115) |
| | Brain meningitis | (196) |
| Eye | Intraocular inflammation | (197) |
| Misc. | Hypertension of the adrenal glands | (198) |
| | Increased expression of P-selectin in breast cancer tissue | (199) |
| | Hyperthyroidism | (121) |
| | Tumor angiogenesis | (200) |

*J. Pediatr. Surg.* 32:1010–1013 (1997); Davenpeck et al., *Am. J. Physiol. Heart Circ. Physiol.* 267:H622–H630 (1994); Gauthier et al., *Am. J. Physiol. Gastrointest. Liver Physiol.* 267:G562–G568 (1994); Weyrich et al., *J. Clin. Invest.* 91:2620–2629 (1993); Tojo et al., *Glycobiology* 6:463–469 (1996); Lefer et al., *Am. J. Physiol. Heart Circ. Physiol.* 271:H2421–H2429 (1996)). Thus, such disorders can be treated using a method of the invention such that the severity of the pathology is reduced. Similarly, acute and chronic inflammatory disorders can be treated using a method of the invention.

For the methods of the invention, an amount of heparin that does not produce substantial anticoagulant activity or undesirable bleeding is administered to the subject. As used herein, reference to "an amount of heparin that does not produce substantial anticoagulant activity" means an amount of heparin that does not cause bleeding complications, although a mild anticoagulant effect can occur. Thus, the amount of heparin administered generally will result in a plasma heparin level of less than about 0.2–0.4 units/ml plasma in a subject.

Clinical signs and symptoms of undesirable bleeding includes blood in the urine, or stool, heavier than normal menses, nose bleeds or excessive bleeding from minor wounds or surgical sites. Easy bruising can precede such clinical manifestations. Where undesirable bleeding occurs, heparin activity can be neutralized by administration of protamine sulfate.

Although an amount of heparin administered to inhibit L-selectin and P-selectin mediated binding in a subject will depend, in part, on the individual, normal adult subjects administered heparin in amounts that result in less than 0.2 units heparin/ml of plasma generally do not exhibit undesirable bleeding. A subject treated with heparin can be monitored for undesirable bleeding using various assays well known in the art. For example, blood clotting time, active partial thromboplastin time (APTT), or anti-Xa activity can be used to determine if coagulation status is undesirably increased in a subject administered heparin. Where undesirable bleeding occurs, heparin administration is discontinued.

The amount of heparin administered depends, in part, on whether L-selectin or P-selectin mediates binding and, therefore, whether only P-selectin, or both L-selectin and P-selectin, are to be inhibited. For example, an amount of heparin less than that used for anticoagulant therapy can be administered to a subject for the purpose of substantially inhibiting P-selectin as compared to L-selectin (see Table 5 and FIGS. 8 and 9). The amount of heparin administered to a subject also depends on the magnitude of the therapeutic effect desired.

In addition, the amount of heparin administered will depend on the individual subject because the bioavailability of heparin within subjects is known to vary. For example, heparin dosages are sometimes administered in units heparin/kg body weight. However, the dosages of heparin needed (e.g. units heparin/kg body weight) to attain specific levels of heparin in the plasma of a subject can vary among individuals because of differences in heparin bioavailability. Thus, the heparin concentration in the blood of a subject in units/ml plasma is the more reliable measure of heparin concentration. The amount of plasma heparin in a subject can be determined using titration and neutralization assays with protamine sulfate.

Heparan sulfate (HS) chains released from endothelial cell heparan sulfate proteoglycans (HSPGs) bind to L-selectin (Norgard-Sumnicht and Varki, *J. Biol. Chem.* 270:12012–12024 (1995)). Selectin-Receptor globulin (Rg) chimeric proteins were used to make affinity columns to determine if these HS ligands also bound to other selectins (P and E). Metabolically labeled HS chains obtained from two endothelial cell lines were applied to each selectin affinity column (see Example I). HS ligand bound primarily to the L-selectin and P-selectin column, but not to the E-selectin column (see FIG. 1). The HS ligand elution profiles using 5 mM EDTA buffer were different; all ligand was released from L-selectin, whereas there was poor release of ligand from P-selectin (see FIG. 1C, inset). Thus, a P-selectin affinity column completely bound the L-selectin HS ligands from both endothelial cell types, but showed a comparatively slow and partial elution with 5 mM EDTA. Addition of 20 mM EDTA resulted in recovery of all of the labeled ligand from both cell sources. This difference in HS elution between the L-selectin and P-selectin columns indicates that the eluting effect of EDTA with P-selectin might not be strictly based upon its calcium chelating properties (see below).

High affinity interactions of selectin generally are dependent on calcium. In addition to calcium, magnesium can potentiate the effects of calcium in P-selectin binding (Geng et al., *Nature* 343:757–760 (1990)). However, the HS ligands studied here are structurally different from the previously described sialylated ligands (Varki, *Proc. Natl. Acad. Sci. USA* 91:7390–7397 (1994); Furie and Furie, *Thromb. Haemost.* 74:224–227 (1995); Vestweber, *J. Clin. Invest.* 98:1699–1702 (1996); McEver et al., *J. Biol. Chem.* 270:11025–11028 (1995); Nelson et al, *Annu. Rev. Cell Biol.* 11:601–631 (1995); Springer, *Annu. Rev. Physiol.* 57:827–872 (1995); Crocker and Feizi, *Curr. Opin. Struct. Biol.* 6:679–691 (1996); Kansas, *Blood* 88:3259–3287 (1996); Rosen and Bertozzi, *Curr. Biol.* 6:261–264 (1996); Vestweber, *J. Cell. Biochem.* 61:585–591 (1996); Varki, *J. Clin. Invest.* 99:158–162 (1997); Phillips et al., *Science* 250:1130–1132 (1990); Walz et al., *Science* 250:1132–1135 (1990); Polley et al., *Proc. Natl. Acad. Sci. USA* 88:6224–6228 (1991); Berg et al., *J. Biol. Chem.* 266:14869–14872 (1991); Tyrell et al., *Proc. Natl. Acad. Sci. USA* 88:10372–10376 (1991); Berg et al., *Biochem. Biophys. Res. Commun.* 184:1048–1055 (1992); Foxall et al., *J. Cell Biol.* 117:895–902 (1992); Larkin et al., *J. Biol. Chem.* 267:13661–13668 (1992); Rosen and Bertozzi, *Curr. Opin. Cell Biol.* 6:663–673 (1994)) and, therefore, an analysis of the calcium dependence of heparan sulfate chain binding to L-selectin and P-selectin was performed.

Figure 2A:
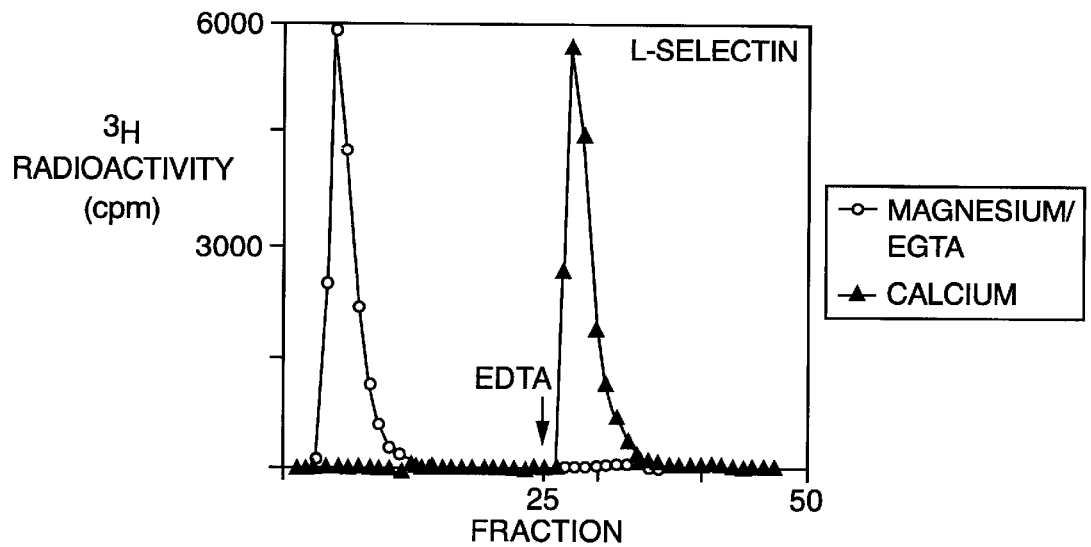
FIG. 2A show that the binding of heparin sulfate glycosaminoglycan chains (HS-GAG) by L-selectin, is calcium-dependent.
Figure 2B:
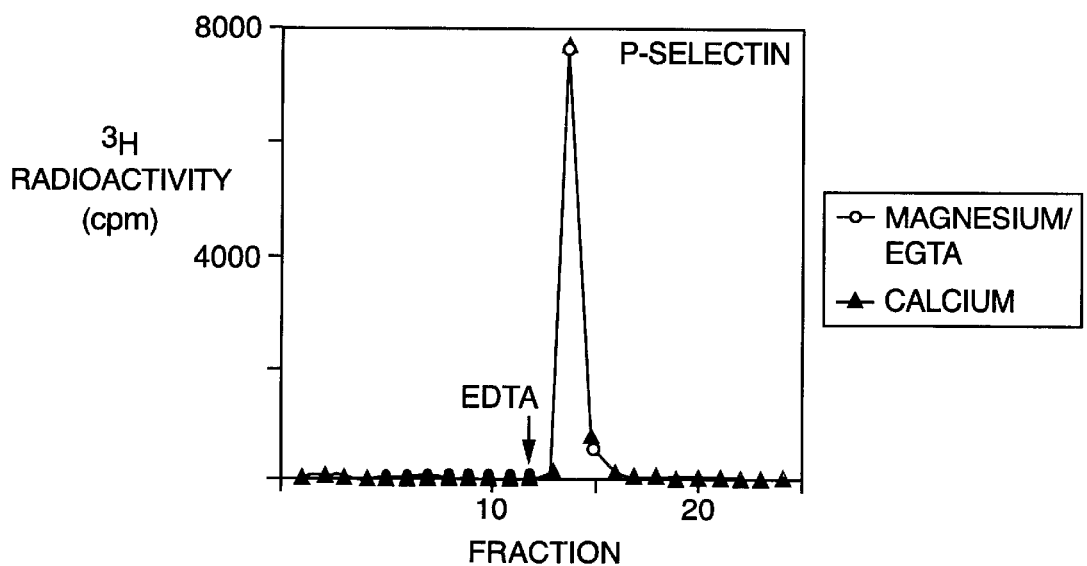
FIG. 2B shows that binding of heparin sulfate glycosaminoglycan chains (HS-GAG) by P-selectin is not calcium-dependent. HS-GAG chains were applied either to an L-selectin or P-selectin column in the presence of 5 mM calcium (solid triangles) or of magnesium/EGTA (open circles). The elution profiles were obtained using 5 mM EDTA buffer for L-selectin and 20 mM EDTA buffer for P-selectin. Arrows as in FIG. 1.
Figure 3:
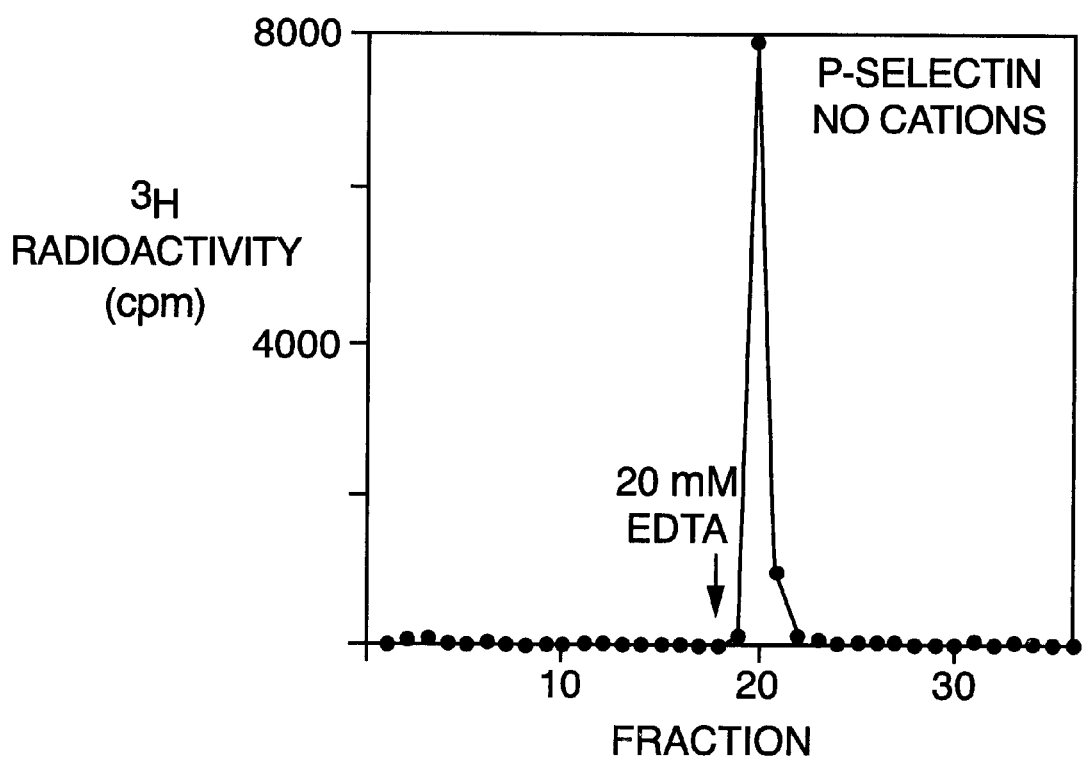
FIG. 3 shows that the binding of the HS-GAG chains to P-selectin does not require exogenously added cations. HS-GAG in buffer lacking exogenously added cations was applied to a P-selectin column, washed with the same buffer and eluted with 20 mM EDTA buffer. Arrows as in FIG. 1.

The calcium dependence of L-selectin binding was determined using binding buffer without added calcium. The binding was not changed, although trace amounts of calcium (approximately 50 $\mu$M) present in a magnesium-containing buffer may support L-selectin binding. Indeed, binding of HS to L-selectin was abolished in magnesium/EGTA buffers, in which calcium was lowered to negligible amounts (FIG. 2A). In contrast, binding of the HS chains to P-selectin occurred in the magnesium/EGTA buffer (FIG. 2B), indicating that HS binds to P-selectin in the absence of exogenously added calcium. FIG. 3 further demonstrates that binding by P-selectin in the absence of exogenously added cations still requires 20 mM EDTA buffer for elution of the HS chains. These results show that although the binding specificities of L-selectin and P-selectin overlap, there are differences, including the different requirement for calcium. However, the presence of calcium in vivo indicates that heparin will inhibit the binding of L-selectin in a subject.

The need for 20 mM EDTA to elute HS chains from the P-selectin column in the absence of divalent cations indicates that either trace amounts of calcium remain tightly bound to the selectin column from the prior experiments or that EDTA is eluting the ligand from P-selectin by a mechanism unrelated to its divalent cation chelating properties. However, it is unlikely that trace amounts of calcium remain tightly bound to the selectin column because crystal structures of E-selectin and the related C-type lectin mannose binding protein indicate that the calcium ion is exposed to the solvent and does not lie deeply buried in the binding pocket (Graves et al., *Nature* 367:532–538 (1994); Weis et al., *Nature* 360:127–134 (1992)). More likely, EDTA is eluting the ligand from P-selectin by a mechanism unrelated to its divalent cation chelating properties because an equivalent (80 mM) increase in chloride concentration did not cause elution. Thus, EDTA can elute the HS ligands due to its inherent polycarboxylate structure, for example, by mimicking the high charge density of HS chains.

HS chains are available in limited quantities so the ability of commercially available mast cell derived PIM-heparin to bind to the selectins was examined (Example II). In addition, PIM-heparin is used as an anticoagulant in humans and its potential use as a selectin therapeutic was of interest. Labeled PIM-heparin in a column buffer adjusted to more closely approximate physiological conditions (Koenig et al., *Glycobiology* 7:79–93 (1997)) was applied to each of the three selectin affinity columns and the bound material was eluted (FIG. 4).

Figure 4A:
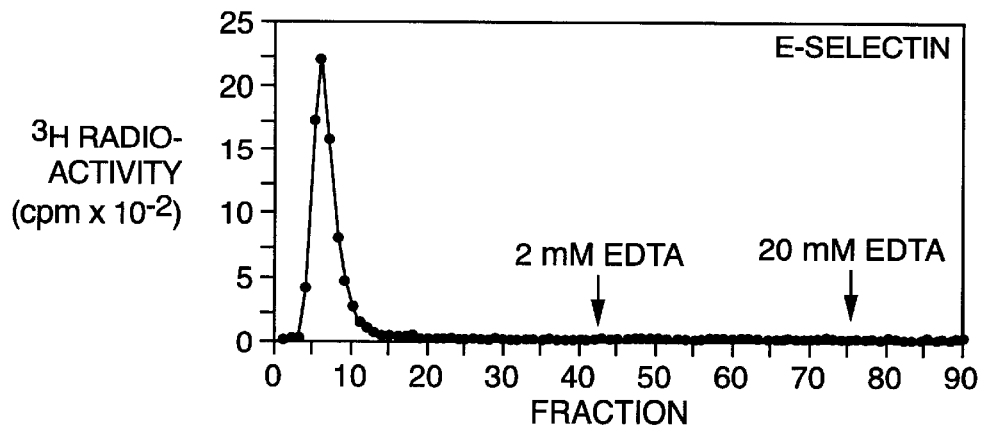
FIG. 4A shows that fractions of porcine intestinal mucosal (PIM) heparin do not bind to E-selectin.
Figure 4B:
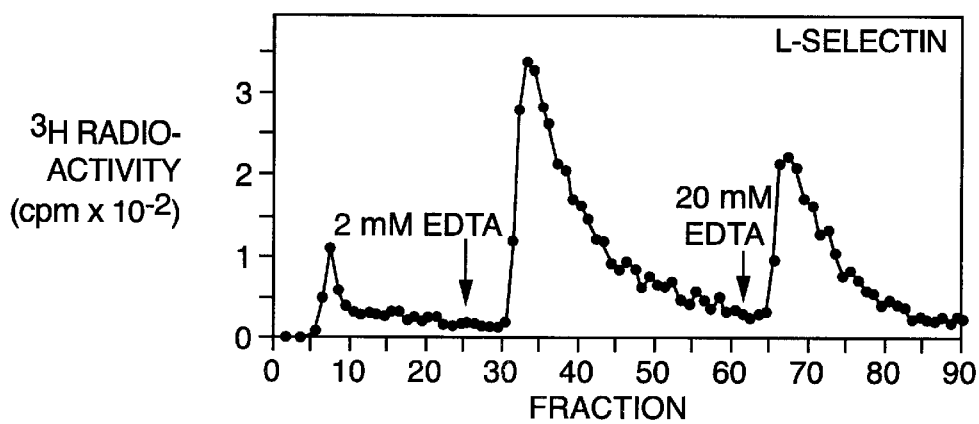
FIG. 4B shows that fractions of porcine intestinal mucosal (PIM) heparin can bind to L-selectin.
Figure 4C:
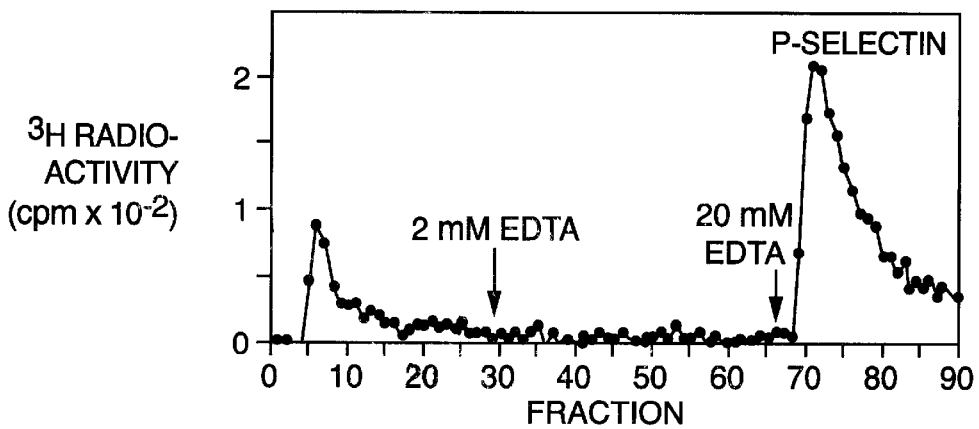
FIG. 4C shows that fractions of porcine intestinal mucosal (PIM) heparin can bind to P-selectin. PIM-Heparin was applied to L-selectin, P-selectin or an E-selectin affinity column; the column was washed and eluted with 2 mM EDTA, followed by 20 mM EDTA buffer.. Arrows as in FIG. 1.

Similar to the results obtained for HS chains, none of the PIM-heparin molecules bound to E-selectin (FIG. 4A). 90% of the total PIM-heparin loaded bound to L-selectin; 58% was eluted with 2 mM EDTA and 32% was eluted with 20 mM EDTA (FIG. 4B). In contrast, 79% of the PIM-heparin bound to P-selectin, very little was eluted with 2 mM EDTA but 20mM EDTA eluted all of the bound heparins (FIG. 4C). These results demonstrate that the binding of PIM-heparin to the selectins was similar to the HS chains obtained from endothelial cells, except that a portion of PIM-heparin remained bound to L-selectin after adding 2 mM EDTA. Thus, heparin compositions commonly formulated for use as anticoagulants have the ability to bind to L-selectin and P-selectin.

Figure 5A:
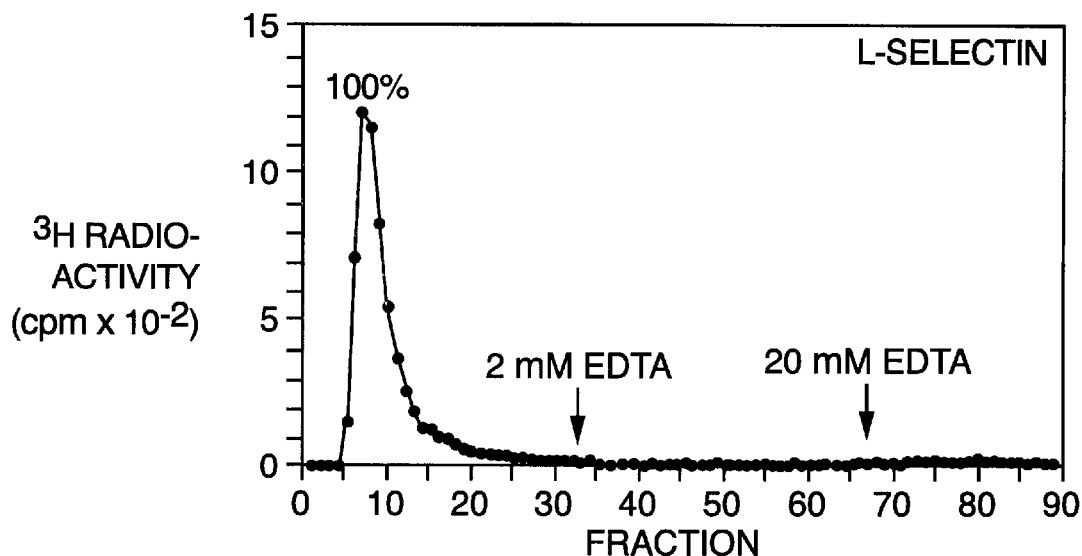
FIG. 5A shows the results of experiments in which the binding of PIM-heparin to L-selectin was shown to be calcium dependent.
Figure 5B:
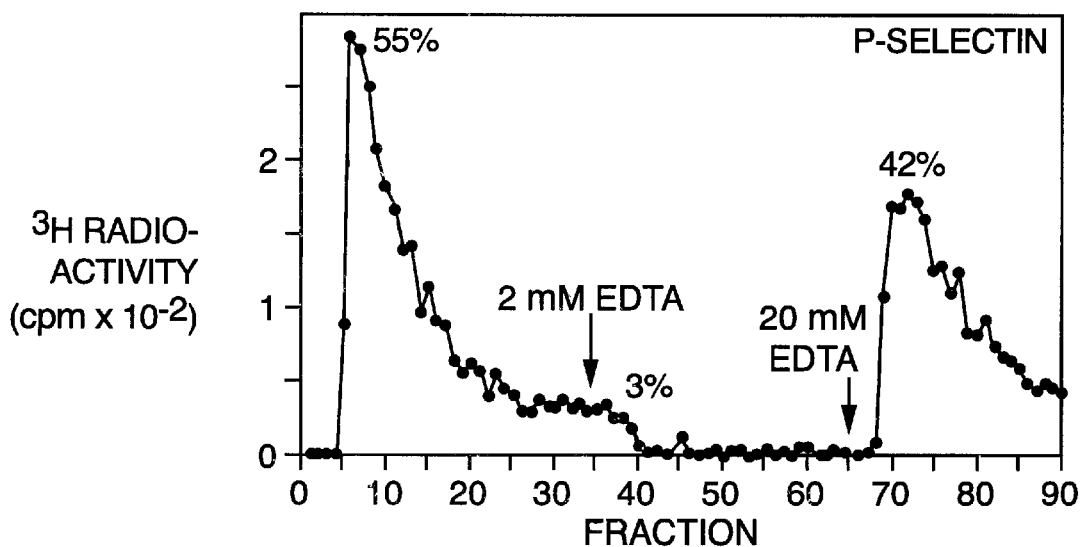
FIG. 5B shows the results for PIM-heparin applied to a P-selectin affinity column. In both of these experiments, the PIM-heparin was applied in a magnesium/EGTA buffer lacking exogenously added calcium. The columns were and eluted with 2 mM EDTA followed by 20 mM EDTA buffer; the percentage eluted in various peaks also is shown. Arrows as in FIG. 1.

The calcium dependence of PIM-heparin binding to L-selectin and P-selectin was similar to the binding of the endothelial HS chains to the selectins (Example II and FIG. 5). Binding to L-selectin was abolished in magnesium/EGTA buffers (FIG. 5A), while a significant fraction continued to bind to P-selectin under these conditions (FIG. 5B). However, the fraction that bound to P-selectin was lower than that seen under calcium-replete conditions (45% vs. 79%), possibly indicating a partial calcium dependency of the initial binding event. Of the fraction that bound in the absence of calcium, 20 mM EDTA was required for elution (FIG. 5B). These results indicate that calcium occupancy in the lectin site may assist the initial binding of some heparin fragments to P-selectin. However, once bound, calcium does not appear to be required to maintain the interaction between the heparin chains and P-selectin.

PIM-heparin chains have a large molecular weight (average 20 kDa; approximately 38–40 disaccharide units) and are polydisperse in structure (Pervin et al., *Glycobiology* 5:83–95 (1995)). In order to determine the specificity of interaction between L-selectin and heparin, the binding of size-fractionated heparin fragments to an L-selectin column was examined (Example III). The binding of PIM-heparin fragments to L-selectin and P-selectin was size dependent; substantial binding occurred with tetradecasaccharides (see FIG. 6D and Table 2). These results indicate that the fraction of PIM-heparin that binds to L-selectin and P-selectin predominantly comprises tetradecasaccharides or larger fragments.

Heparin tetrasaccharides interact with L-selectin in blocking binding to immobilized sialyl-Lewis$^x$ (SLe$^x$; Siao2–3 Galβ1–4 (Fucal-3) GlcNAc), a well known component of natural selectin ligands (Nelson et al., supra, 1993). Studies of other oligosaccharide protein interactions indicate that binding constants in the low $\mu$M range would be needed for the detection of selectin binding (Varki and Kornfeld, *J. Biol. Chem.* the selectin-Rg chimeras (Graves et al., supra, 1994). The tetradecasaccharides were generated by partial heparin lyase I degradation and reduced with borohydride which results in the first, or nonreducing, monosaccharide unit having a non-native C4–C5 double bond, and the last unit having an open ring. Consistent with the results discussed above, the binding to L-selectin was disrupted by 2 mM EDTA and was calcium dependent whereas the binding to P-selectin was calcium independent. The crystal structure of the closely related molecule E-selectin indicated that the putative carbohydrate binding region of the lectin domain is located on the opposite face from the EGF domain. Thus, despite the lack of calcium dependence of binding of the tetradecasaccharides to P-selectin, these molecules may be binding somewhere relatively close to the calcium dependent binding site for SLe$^x$.

TABLE 2

Unfractionated and LMW Heparins as
Inhibitors of L- and P-Selectin binding to Immobilized SLc$^x$ and to [$^3$H] HL-60 cells.

| | Therapeutic range (Units/ml)* | IC$_{50}$ Units/ml* | | | | |
|---|---|---|---|---|---|---|
| | | Against immobilized SLc$^x$ | | | Against HL-60 cells | |
| Clinical heparin | | E-Selectin | L-Selectin | P-Selectin | L-Selectin | P-Selectin |
| Unfractionated Heparin | 0.2–0.4 | >50 | 0.07–0.08 | 0.01–0.02 | 0.02–0.03 | 0.003–0.01 |
| Levonox (LMW Heparin, Enoxaparin) | 0.6–1.0 | >50 | 0.8–1.5 | 0.8–1.0 | 1.5–3.0 | 0.7 |
| Fragmin (LMW Heparin, Deltaparin) | 0.6–1.0 | >50 | 0.7–2.0 | 1.5–2.0 | 4.0–7.0 | 1.0–4.0 |

Several clinical lots of Unfractionated and LMW Heparins were tested for their ability to inhibit selectin binding to immobilized Sle$^x$ in ELISA inhibition experiments or HL-60 cells binding to immobilized selectins, as described under "Materials and Methods." IC$_{50}$ values were determined by the equation: {[(average of duplicates)−(average of negative controls)]/[(average of positive controls)−(average of negative controls)]}×100, where the positive controls were without inhibitors, and the negative controls contained 5 mM EDTA in the ELISA inhibition experiments, and 20 mM EDTA in the HL-60 cell inhibition experiments. Experiments were performed 2-times, and the range of measured IC$_{50}$ values are presented. Examples of the results can be seen in FIGS. 1 and 2. Unfractionated heparin concentrations are reported in Protamine neutralization Units while LMW heparins are reported as anti-Xa Units (see text for discussion). 258:2808–2818 (1983); Powell et al., *J. Biol. Chem.* 270:7523–7532 (1995)). ELISA inhibition experiments using immobilized SLe$^x$ demonstrated that the PIM-heparin tetradecasaccharides had a calculated IC$_{50}$ value of 82 $\mu$M and 54 $\mu$M for L-selectin and P-selectin binding, respectively (see Example IV and Table 3). These IC$_{50}$ values are almost 10-fold less than those reported for Sle$^x$ itself (520 $\mu$M and 600 $\mu$M for P-selectin and L-selectin, respectively). These results demonstrate that the tetradecasaccharides bind L-selectin and P-selectin with greater affinity than SLe$^x$.

Given the size of the tetradecasaccharides relative to that of the selectin lectin domain, the interactions with tetradecasaccharides likely represent monovalent recognition by

TABLE 3

Heparin Fragment Mixtures as
Inhibitors of L- and P-Selectin binding to Immobilized SLc$^x$.

| | IC$_{50}$ value | |
|---|---|---|
| | L-Selectin | P-Selectin |
| Tetradecasaccharides | 54 uM | 82 uM |
| Dodecasaccharides | 159 uM | 159 uM |
| Decasaccharides | >1900 uM | >1900 uM |
| Octasaccharides | >2400 uM | >2400 uM |
| Sialyl Lewis$^x$ | 600 uM | 520 uM |

Size-fractionated PIM-heparin mixtures were tested for their ability to inhibit selectin binding to immobilized SLe$^x$ in ELISA inhibition experiments, as described under "Materials and Methods." There was no inhibition of E-selectin, even with the tetradecasaccharides, at concentrations as high as 5 mg/ml (>1000 uM). IC$_{50}$ values for L- and P-selectin inhibition were determined by the equation: {[(average of duplicates)−(average of negative controls)]/[(average of positive controls)−(average of negative controls)]}*100, where the positive controls were without inhibitors, and the negative controls contained 5 mM EDTA. Experiments were performed 2–3 times, and the averaged IC$_{50}$ values are presented. For calculation or concentration, the following average molecular weights were assumed: tetradecasaccharide, 3675 Da; dodecasaccharide, 3150 Da; decasaccharide, 2625 Da; and octasaccharides, 2100 Da. The inhibitory potency of the tetrasaccharide Sialyl Lewis$^x$ under the same conditions is shown for comparison.

With the availability of a size defined fraction, the binding of some molecules and the lack of binding of others indicates a degree of specificity. Such specificity was confirmed by performing rebinding experiments with the tetradecasaccharide pooled fractions were performed (Example III). For both L-selectin and P-selectin, the binding of the fractions was reproducible (see FIG. 7, for L-selectin, and Table 4). The divalent cation dependence of this interaction also was similar to that of intact heparin and the endothelial HS chains. In addition, the interactions with L-selectin were disrupted by 2 mM EDTA (FIG. 7), whereas those with P-selectin required 20 mM EDTA for disruption (Table4) and studies with magnesium/EGTA buffers confirmed the calcium dependency of L-selectin binding. These results demonstrate that various ligand populations differ over a wide range in their ability to interact with L-selectin. Thus, individual heparin chains or pools of related chains are likely to exhibit differential affinity for selecting. Such ligands that selectively bind are useful for the selective targeting of selectins in vivo.

In an effort to determine if there are differences between the types of tetradecasaccharides that are recognized by L-selectin and P-selectin, cross-binding studies were performed (Example III). Of the tetradecasaccharides that bound to L-selectin, 100% bound to P-selectin and were eluted with 20 mM EDTA (see Table 4). In contrast, not all of the tetradecasaccharides that bound to P-selectin also bound to L-selectin. Of the tetradecasaccharides from the P-selectin column that bound to L-selectin, 22% were from the 2 mM EBTA eluted fraction and 51% were from the 20 mM DTA eluted fraction. Of the fraction that did not bind P-selectin and L-selectin columns were cleaved, and the products analyzed by FPLC (Example III). L-selectin binding fragments were more heavily sulfated and epimerized and, similar to the endothelial HS chains, they were enriched in free amino groups. The P-selectin binding component included this fraction as well as some less highly modified regions; they were sensitive to Heparin Lyase III. These results indicate that, while distinct structural features selectively enhance interactions of P-selectin and L-selectin with heparin tetradecasaccharides, the binding represents a continuum of affinities with no apparent structural motif being markedly superior in its ability to be recognized.

The clinical relevance of the observations made using commercially available PIM-heparin, which is very similar to the heparin used as an anticoagulant (Ginsberg, *N. Engl. J. Med.* 335:1816–1828 (1996); Hirsh, *Semin. Thromb. Hemost.* 22 Suppl:7–12 (1996); Pineo and Hull, *Annu. Rev. Med.* 48:79–91 (1997)) were analyzed further. ELISA inhibition studies using immobilized SLe$^x$ indicated that crude commercial PIM-heparin had an IC$_{50}$ of 18 μg/ml and 2 μg/ml for SLe$^x$ binding to L-selectin and P-selectin, respectively. Although crude heparin preparations vary between lots, the IC$_{50}$ values for crude PIM-heparin roughly corresponds to pharmaceutical heparin preparations of approximately 0.18–0.09 units/ml (L-selectin) and 0.02–0.01 units/

TABLE 4

Rebinding and cross-binding of Tetradecasaccharides to L- and P-selectin

| | Original Binding of sample | | | | |
|---|---|---|---|---|---|
| Secondary Binding | L-selectin unbound | L-selectin 2 mM EDTA eluted | P-selectin unbound | P-selectin 2 mM EDTA eluted | P-selectin 20 mM EDTA eluted |
| L-selectin | | | | | |
| Unbound | 98% | 0% | 100% | 78% | 49% |
| 2 mM EDTA eluted | 2% | 100% | 0% | 22% | 51% |
| P-selectin | | | | | |
| Unbound | 88% | 0% | 88% | 0% | 0% |
| 2 mM EDTA eluted | 0% | 0% | 5% | 100% | 0% |
| 20 mM EDTA Eluted | 12% | 100% | 7% | 0% | 100% |

[$^3$H]-labeled tetradeccasaccharides were fractionationed by P- and L-selectin affinity chromatography as described under "Materials and Methods"). After desalting, aliquots of each fraction were reapplied to the same column, or to the other selectin column, (see FIG. 7 for an example of the results). to L-selectin, 12% re-bound to P-selectin. These data indicate that, although both L-selectin and P-selectin exhibit some degree of selectivity, L-selectin has a greater degree of selectivity than P-selectin in binding heparin tetradecasaccharides. Thus, in view of this greater selectivity, L-selectin can be targeted over P-selectin using particular tetradecasaccharide fractions.

Since the size of the recognized tetradecasaccharides is not a variable, the differences in affinity are a result of structural differences between them. The structures of the tetradecasaccharides were examined using enzymes or chemical modification that cleave the chains at particular sites (Lohse and Linhardt, *J. Biol. Chem.* 267:24347–24355 (1992); Conrad, *In Current Protocols in Molecular Biology* 17–22A (1996); Desai et al., *Biochemistry* 32:8140–8145 (1993); Jandik et al., *Glycobiology* 4:289–296 (1994); Linhardt, *In Current Protocols in Molecular Biology* 17–18B (1996)). Bound and flow-through material from the ml (P-selectin). These results indicate that the inhibition of binding can occur at therapeutically relevant concentrations.

In order to understand the relevance of these studies to clinical practice, the effect of pharmaceutical heparin preparations on selectin binding was determined (Example IV). ELISA inhibition assays (see FIG. 8 and Table 5) demonstrated that two separate lots of pharmaceutical unfractionated heparin significantly inhibited L-selectin and P-selectin, but not E-selectin, binding at concentrations less than that recommended for anticoagulation therapy (Table 5). The calculated IC$_{50}$ values towards SLe$^x$ binding were 0.07–0.08 units/ml for L-selectin and 0.01–0.02 units/ml for P-selectin (Table 5).

Similar findings were obtained in an HL-60 cell attachment assay, which measured the interaction of L-selectin and P-selectin with the natural selectin ligand PSGL-1 expressed by the HL-60 cells (Example IV). PSGL-1 is a primary selectin ligand with significant

TABLE 5

Unfractionated and LMW Heparins as
Inhibitors of L- and P-Selectin binding to Immobilized SLc$^x$ and to [$^3$H] HL-60 cells.

| Clinical heparin | Therapeutic range (Units/ml)* | IC$_{50}$ Units/ml* | | | | |
|---|---|---|---|---|---|---|
| | | Against immobilized SLc$^x$ | | | Against HL-60 cells | |
| | | E-Selectin | L-Selectin | P-Selectin | L-Selectin | P-Selectin |
| Unfractionated Heparin | 0.2–0.4 | >50 | 0.07–0.08 | 0.01–0.02 | 0.02–0.03 | 0.003–0.01 |
| Levonox (LMW Heparin, Enoxaparin) | 0.6–1.0 | >50 | 0.8–1.5 | 0.8–1.0 | 1.5–3.0 | 0.7 |
| Fragmin (LMW Heparin, Deltaparin) | 0.6–1.0 | >50 | 0.7–2.0 | 1.5–2.0 | 4.0–7.0 | 1.0–4.0 |

Figure 8A:
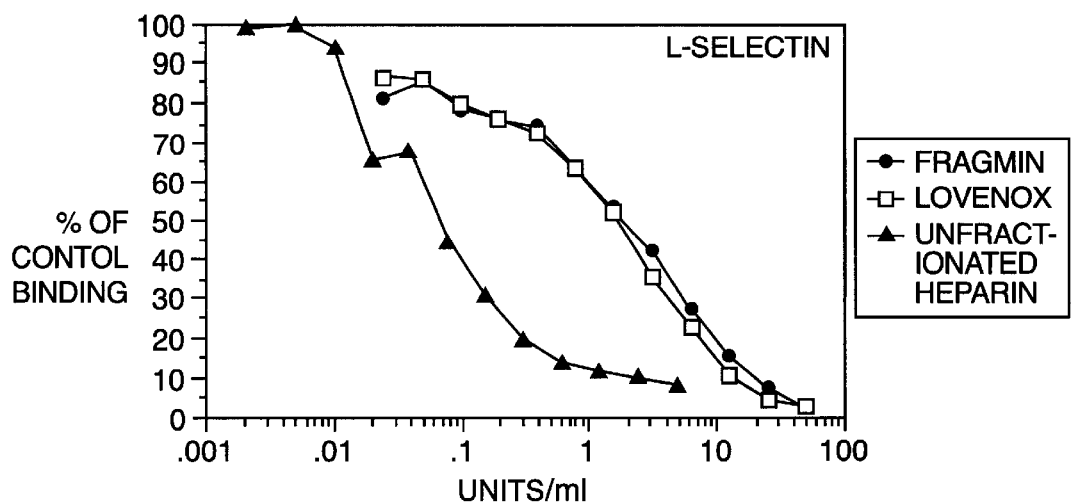
Figure 8B:
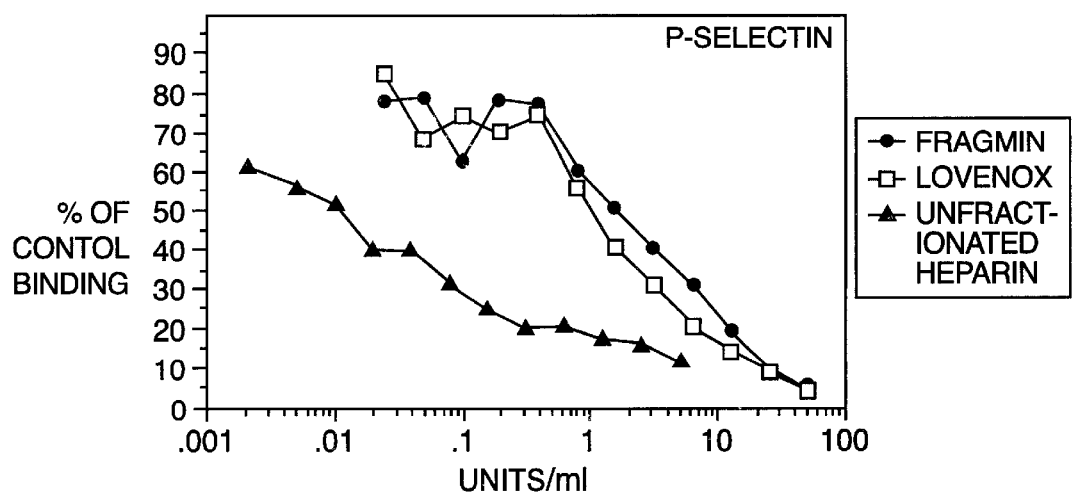
FIG. 8B shows the inhibitory properties of a pharmaceutical heparin preparation (unfractionated; closed triangles) or LMW heparins (LOVENOX, open squares; FRAGMIN, closed circles) on the binding of P-selectin to immobilized SLe* using ELISA inhibition experiments. "Units/ml" indicates that concentration of heparin or LMW heparins in the reaction.
Figure 9:
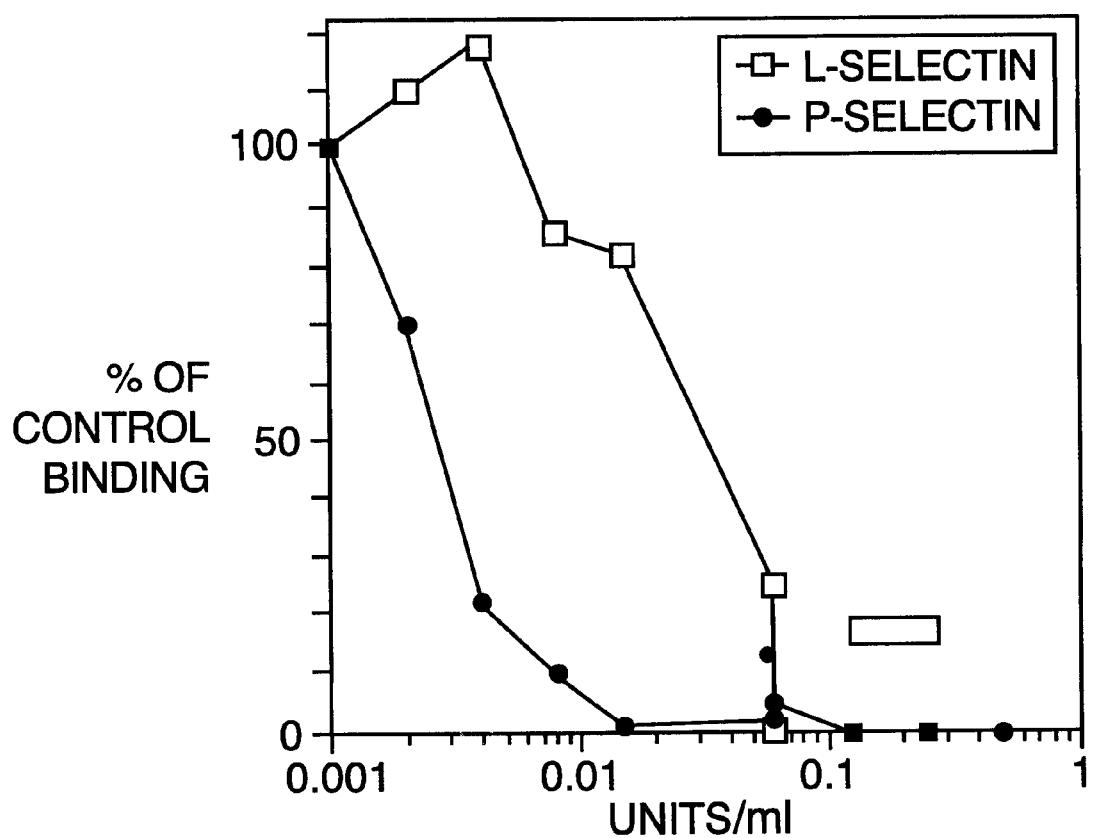
FIG. 9 shows the inhibition of HL-60 cell attachment to immobilized L-selectin (open squares) or P-selectin (closed circles) by a pharmaceutical heparin preparation (unfractionated). The horizontal bar indicates the recommended plasma concentration range for therapeutic use of heparin as an anticoagulant in a human subject.

Several clinical lots of Unfractionated and LMW Heparins were tested for their ability to inhibit selectin binding to immobilized SLe$^x$ in ELISA inhibition experiments or HL-60 cells binding to immobilized selectins, as described under "Materials and Methods." IC$_{50}$ values were determined by the equation: {[(average of duplicates)–(average of negative controls)]/[(average of positive controls)–(average of negative controls)]}×100, where the positive controls were without inhibitors, and the negative controls contained 5 mM EDTA in the ELISA inhibition experiments, and 20 mM EDTA in the HL-60 cell inhibition experiments. Experiments were performed 2–3 times, and the range of measured IC$_{50}$ values are presented. Examples of the results can be seen in FIGS. 8 and 9. Unfractionated heparin concentrations are reported in Protamine neutralization Units while LMW heparins are reported as anti-Xa Units (see text for discussion). biological relevance in vivo (Kansas, supra, 1996; Rosen and Bertozzi, supra, 1996; Vestweber, supra, 1996; Lowe and Ward, *J. Clin. Invest.* 99:822–826 (1997); Varki, supra, 1997; McEver and Cummings, *J. Clin. Invest.* 100:485–492 (1997)). The binding of HL-60 cells to L-selectin and to P-selectin was inhibited by unfractionated pharmaceutical heparin (FIG. 9). The IC$_5$ values calculated for HL-60 binding to L-selectin and P-selectin were approximately 12-fold and 50-fold lower, respectively, than the recommended range for anticoagulant therapy (Table 5).

Pharmaceutical preparations of low molecular weight (LMW) heparins different from those described by Bevilacqua et al. have been used for anticoagulant therapy in place of unfractionated heparin due to enhanced bioavailability and half-life and a somewhat decreased degree of toxicity (Ginsberg, supra, 1996; Hirsch, supra, 1996; Sakuragawa and Takahashi, *Semin. Thromb. Hemost.* 16 Suppl.:5–11 (1990); Pineo and Hull, supra, 1997; Boneu, *Semin. Thromb. Hemost.* 22:209–212 (1996)). The ability of two kinds of clinical grade LMW heparins, FRAGMIN (Pharmacia-Upjohn; Kalamazoo Mich.) and LOVENOX (Rhone-Poulenc Rorer; Collegeville Pa.), to inhibit selectin binding was compared to unfractionated pharmaceutical heparin (FIG. 8). The IC$_{50}$ values of the LMW heparins for L-selectin and P-selectin binding were at or higher than the recommended therapeutic levels of unfractionated heparin in ELISA inhibition experiments against immobilized SLe$^x$ and in HL-60 cell attachment inhibition experiments (Table 5). Thus, the two LMW heparins are much poorer inhibitors of L-selectin and P-selectin binding to sialylated ligands, including the naturally occurring PSGL-1 ligand, than unfractionated pharmaceutical heparin. The difference in binding inhibition between unfractionated and LMW heparins appears to be due to smaller sized heparin fragments having less affinity or avidity for the selectins (see FIG. 6).

The results disclosed herein demonstrate that L-selectin and P-selectin binding to SLe$^x$ and to PSGL-1 of HL-60 cells is inhibited by unfractionated pharmaceutical heparin preparations at concentrations 12-fold to 50-fold lower than those recommended for effective anticoagulation in vivo. These results indicate that patients undergoing heparin anticoagulant therapy can experience clinically significant inhibition of L-selectin and P-selectin function. However, the current switch from unfractionated heparin to low molecular weight anticoagulant forms of heparin likely results in a significant loss of the selectin inhibitory effect due to the decreased ability of LMW heparins to inhibit L-selectin and P-selectin binding. This relative lack of affinity may be due to selectins favoring higher order carbohydrate structures. As disclosed herein, administration of low dose unfractionated heparin provides a treatment option for acute and chronic diseases involving P-selectin or L-selectin mediated binding, particularly administration of heparin in an amount that does not produce substantial anticoagulant activity or undesirable bleeding in a subject.

Although SLe$^x$ and related structures may be therapeutically useful in a variety of disease states (Albelda et al., *FASEB J.* 8:504–512 (1994); Lowe and Ward, supra, 1997; Weyrich et al., *J. Clin. Invest.* 91:2620–2629 (1993); Ridings et al., *J. Appl. Physiol.* 82:644–651 (1997); Bevilacqua et al., *Annu. Rev. Med.* 45:361–378 (1994); Skurk et al., *Am. J. Physiol. Heart Circ. Physiol.* 267:H2124–H2131 (1994); Lefer, *Ann. Thorac. Surg.* 60:773–777 (1995); Seekamp and Ward, *Agents Actions* 41:137–152 (1993)), they have a number of significant drawbacks. As disclosed herein, the affinity of pharmaceutical compositions of unfractionated heparin for L-selectin and P-selectin is higher than that of oligosaccharides such as SLe$^x$ (Table 3), LOVENOX and FRAGMIN (Table 5 and FIG. 8). In particular, the IC$_{50}$ calculated for inhibition of HL-60 cell attachment to L-selectin using unfractionated heparin is approximately 10-fold less than the recommended levels for anticoagulation (Table 5). The IC$_{50}$ values for P-selectin are even lower, and are approximately 50-fold less than the recommended therapeutic level for anticoagulant activity. Thus, the recommended level of unfractionated heparin for anticoagulation can completely inhibit L-selectin and P-selectin mediated binding in an in vitro binding assay.

In addition to FRAGMIN and LOVENOX, other forms of LMW heparins used for anticoagulant therapy are commercially available. As disclosed herein, these other LMW heparins also can be useful for inhibiting selectin binding at concentrations less than those used for anticoagulant therapies. Such forms of LMW heparin formulated for clinical use in anticoagulant therapies, therefore, also can be used in a method of the invention.

Many reperfusion injury situations such as those occurring in stroke and myocardial ischemia, in which inhibition of PSGL-1 based P-selectin and L-selectin interactions are a potential target (Table 1), are routinely treated with anticoagulating amounts of heparin with the intention of preventing further thrombosis. As disclosed herein, a result of administering these amounts of heparin is that clinicians may have inadvertently inhibited selectin mediated binding. Consistent with this view, the best effects of thrombolytic therapy for acute myocardial infarction occurs when heparin is included in the treatment regimen. The results disclosed herein indicate that heparin can provide protection from reperfusion injury by inhibiting P-selectin and L-selectin mediated binding.

The results disclosed herein, along with the established record of heparin as a therapeutic agent, indicate that heparin can be useful for inhibiting L-selectin or P-selectin based interactions using amounts lower than those required for anticoagulant therapy. Thus, the invention provides a method of inhibiting L-selectin or P-selectin binding in a subject, by administering to the subject an amount of heparin that does not produce substantial anticoagulant activity or undesirable bleeding in the subject. Further provided are methods of treating an L-selectin or P-selectin related pathology by administering to a subject having the pathology an amount of heparin that does not produce substantial anticoagulant activity or undesirable bleeding in the subject.

Particular acute and chronic conditions, in which P-selectin or L-selectin have a pathophysiological role can be treated using a method of the invention (Table 1). For example, undesirable immune responses in which the homing or adhesion of leukocytes, neutrophils, macrophages, eosinophils or other immune cells mediated by the interaction of L-selectin with endothelial cell ligands, can be inhibited by administering heparin to the subject according to a method of the invention. Inhibition of neutrophil adherence, for example, can interrupt the cascade of damage initiated by free oxygen radical secretion and related activities that result in tissue damage and loss of myocardial contractile function present in myocardial infarction. Similarly, P-selectin mediated adhesion of cells such as neutrophils and platelets can be inhibited in a subject if this activity is undesirable. Thus, the severity of chronic immune disorders or acute inflammatory responses can be reduced using a method of the invention.

When administered to a subject, heparin is administered as a pharmaceutical composition. Such pharmaceutical compositions of heparin are commercially available and protocols for heparin administration are wellknown in the art. Such compositions and administration protocols can be conveniently employed in practicing the invention. One skilled in the art would know that the choice of the particular heparin pharmaceutical composition, depends, for example, on the route of administration and that a pharmaceutical composition of heparin can be administered to a subject by various routes., including, for example, parenterally, particularly intravenously. The heparin composition can be administered by intravenous or subcutaneous injection, and administration can be as a bolus or by continuous infusion. In addition, mucosally absorbable forms of heparin can be administered orally, rectally or by inhalation, provided the amount of heparin attained in the blood does not exceed a concentration of about 0.2–0.4 units/ml plasma and does not produce substantial anticoagulant activity or undesirable bleeding in the subject.

Depending on the commercial source, pharmaceutical preparations of heparin for injection are supplied at concentrations from 1000 units/ml to 20,000 units/ml (Eli Lilly, Indianapolis Ind.; Elkins-Sinn, Inc., Cherry Hill N.J.; Wyeth-Ayerst Laboratories, Philadelphia Pa.; Pharmacia-Upjohn, Kalamazoo Mich.). Thus, pharmaceutical heparin preparations that are about one-fifth to one-tenth as concentrated can be used for administration to a subject in order to inhibit L-selectin or P-selectin mediated binding in the subject. For example, heparin pharmaceutical compositions of about 250–950 units/ml or 50–250 units/ml, or less can be prepared and used in the methods of the invention. Thus, the invention provides pharmaceutical compositions comprising less than 1000 units heparin/ml. Dilutions of more concentrated commercially available pharmaceutical heparin to achieve these lower concentrations of heparin also are provided.

The following examples are intended to illustrate but not limit the present invention.

EXAMPLE I

Binding of Heparan Sulfate Chains to L-Selectin and P-Selectin

This example demonstrates that heparan sulfate (HS) chains from endothelial cells bind to L-selectin and P-selectin.

A. Endothelial Heparan Sulfate Ligands for L-selectin also Bind to P-selectin but not to E-selectin Affinity columns containing the L-selectin, P-selectin and E-selectin chimeric proteins were used to determine whether HS ligands released from endothelial cell HSPGs that bind to L-selectin, also can bind other selectins. Recombinant selectin chimeras consisting of L-selectin-Rg, P-selectin-Rg and E-selectin-Rg were produced as previously described (Norgard et al., *Proc. Natl. Acad. Sci. USA* 90:1068–1072 (1993); Aruffo et al., *Proc. Natl. Acad. Sci. USA* 89:2292–2296 (1992); Nelson et al., *J. Clin. Invest.* 91:1157–1166 (1993)). Affinity columns were prepared by immobilizing 0.5 mg of each selectin-Rg on 0.5 ml of protein A-SEPHAROSE (PAS; Sigma, St. Louis Mo.).

CPAE cells, a calf pulmonary artery endothelial cell line (ATCC Accession No. CCL 209), were used at or before passage 23 as a source of HS chains and were grown to 80% confluence. Human umbilical vein endothelial cells (HUVECs; Clonetics, San Diego Calif.) were used within the first 3 passages and also provided a source of HS chains. CPAE and HUVECcells were labeled with ($^3$H)GlcNH$_2$ (60 Ci/mmol; American Radiolabeled Chemicals, St. Louis Mo.) and the free HS chains were released from the ($^3$H)GlcNH$_2$ labeled cell proteoglycans and purified as described previously (Norgard-Sumnicht et al., supra, 1993; Norgard-Sumnicht and Varki, supra, 1995; Roux et al., *J. Biol. Chem.* 263:8879–8889 (1988)). Similar amounts of the labeled HS chains in 100 mM NaCl, 20 mM MOPS (pH 7.4), 1 mM CaCl$_2$, 1 mM MgCl$_2$ buffer were applied to each column. After washing the column, bound ligand was eluted using the above binding buffer, except CaCl$_2$ and MgCl$_2$ were replaced with 5 mM EDTA.

Figure 1B:
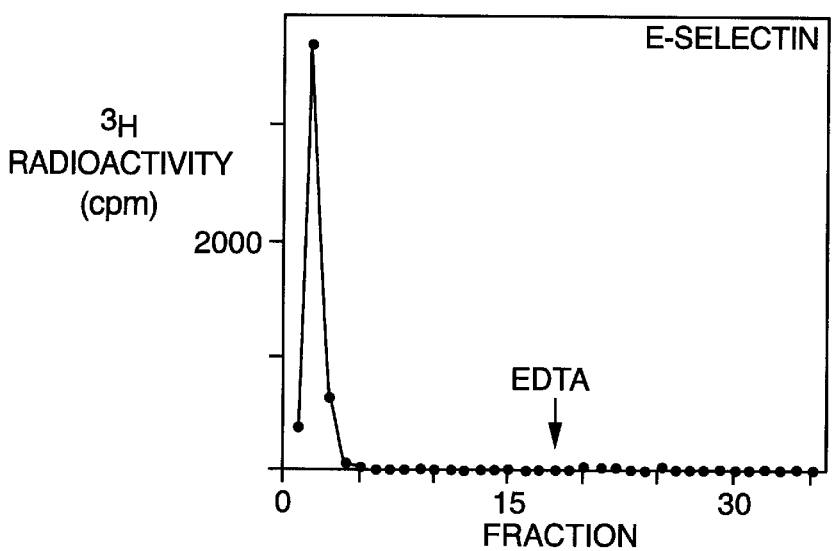
FIG. 1B shows that heparin sulfate obtained from endothelial cells does not bind to E-selectin.
Figure 1C:
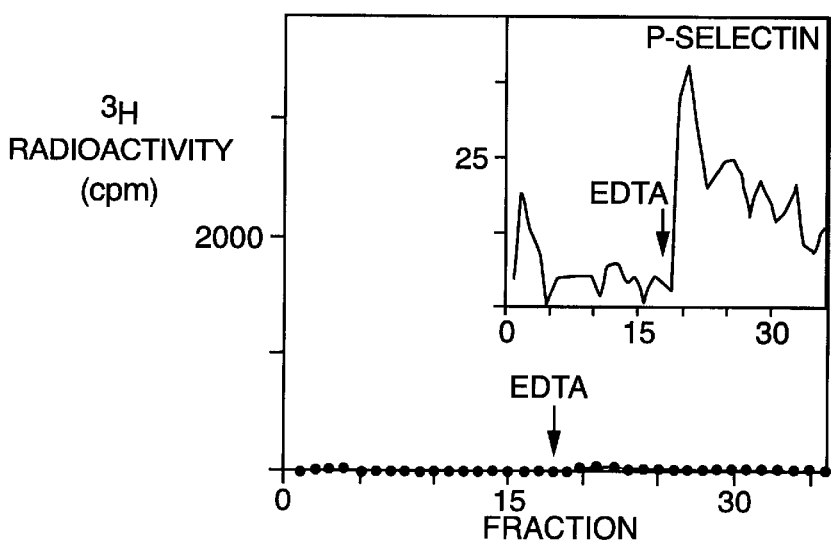
FIG. 1C shows that heparin sulfate obtained from endothelial cells binds to P-selectin. The elution profile of HS chain from an L-selectin, P-selectin or E-selectin affinity column using buffer containing 5 mM EDTA is shown. Arrows indicate fraction where EDTA elution began.

Most of the HS ligand rebound to the L-selectin column and was eluted with 5 mM EDTA (FIG. 1A). The HS ligand also bound to the P-selectin column, however, it eluted very poorly with 5 mM EDTA (FIG. 1C, inset). Subsequent elution with binding buffer in which CaCl$_2$ and MgCl$_2$ was replaced with 20 mM EDTA resulted in recovery of all of the HS ligand from the P-selectin column. In contrast, no binding to the E-selectin column was detected (FIG. 1B), although the E-selectin column did bind other ligands from carcinoma cells in a calcium-dependent manner and, therefore, was functional. ($^{35}$S)-labeled HS chains from CPAE cells and labeled HS chains from HUVEC cells provided similar binding profiles to the L-selectin and P-selectin columns.

These results demonstrate that HS ligands obtained from CPAE and the HUVEC cells bound the L-selectin and P-selectin columns, but not E-selectin column.

B. Comparison of Calcium Dependence of Heparan Sulfate Chain Binding to L-selectin and P-selectin The calcium dependence of the HS chain interaction with L-selectin and P-selectin was determined. Aliquots of HS chains that previously bound to an L-selectin column were reapplied either to the same column or to a P-selectin column. The columns were washed, eluted with either 5 mM EDTA for L-selectin or 20 mM EDTA for P-selectin, and the fractions collected and monitored for radioactivity (FIG. 2).

Omission of calcium from the binding buffer did not change the results, although calcium (approximately 50 μM) present in the 2 mM magnesium containing buffer may support L-selectin binding. The binding of HS chains to L-selectin was abolished in $Mg^{++}$/EGTA buffers, in which calcium is present in negligible amounts (effective $Ca^{++}$ concentration 0.774 nM, $Mg^{++}$ concentration 3 mM; FIG. 2). The calcium dependence of the L-selectin interaction was confirmed by demonstrating that 0.5 mM EDTA efficiently eluted HS chains from the L-selectin column (FIG. 2A). In contrast to L-selectin, binding of the HS chains to P-selectin occurred even in the magnesium/EGTA buffer (see FIG. 2B, indicating that HS binding to P-selectin did not require exogenously added calcium.

Since the binding of the HS chains to P-selectin occurred in the presence of either calcium or magnesium, the binding requirements for exogenously added cations was determined. An aliquot of the HS-GAG ligand that had previously bound to an L-selectin column was dialyzed against water, then was adjusted into buffer containing 100 mM NaCl, 20 mM MOPS (pH 7.4). The P-selectin column was prepared by washing with 20 mM EDTA, incubating in 20 mM EDTA overnight at 4° C., then extensively washing with the MOPS/NaCl buffer. The HS-GAG aliquot was applied to the P-selectin column, washed with the same buffer and eluted with 20 mM EDTA. The fractions were collected and monitored for radioactivity.

Binding to P-selectin occurred in the absence of exogenously added cations (FIG. 3); however, the ligand was eluted with 20 mM EDTA. These results show that L-selectin binding is divalent cation dependent, whereas P-selectin binding does not require exogenously added divalent cations.

EXAMPLE II

Binding of Porcine Mucosal Heparin to L-Selectin and P-Selectin

This example demonstrates that porcine intestinal mucosal (mast cell-derived) heparin (PIM-heparin) binds to L-selectin and P-selectin.

A. PIM-heparin Shows Similar, but not Identical, Binding to the Selecting

The binding of commercially available PIM-heparin (Sigma, St. Louis Mo.) to L-selectin and P-selectin was analyzed. Briefly, the large heparin, chains in this preparation were radiolabeled by adding a 5-fold molar excess of $NaB(^3H)_4$ (approximately 1.4 to 7 mCi) to about 20 to 120 nmoles of di- to tetradeca-saccharide heparin in 100 μl of 0.2 M sodium borate buffer, pH 10. The reaction proceeded for 4 hours at room temperature and 40 μl of 1 M $NaBH_4$ was added. After one hour, 40 μl of acetone was added to quench the reaction. The next day, the samples were treated with 150 μl of 1.0 M ammonium formate buffer and stored at −80° C. until use.

Thawed samples were desalted using Bio-Gel P-2 columns (Bio-Rad, Hercules Calif.) in 100 nM ammonium formate buffer, pH 5. The void volume (Vo) and included volume (Vi) were determined by loading 400 μl 0.1% blue dextran (detected by color) in 100 mM ammonium formate buffer, pH 5, plus 200 mM NaCl (detected with $AgNO_3$). Samples were eluted with 100 nM ammonium formate buffer, pH 5, into 500 μl fractions containing the Vo($^3H$) cpm which were pooled, lyophilized, dissolved in $H_2O$, and stored at −20° C. SEPHADEX G-15 chromatography was used to remove additional contaminants.

Selectin affinity columns having a ratio of 1.7 mg of selectin-Rg to 1 ml PAS were prepared and used for the PIM-heparin studies. Aliquots of $^3H$-labeled PIM-Heparin were applied to L-selectin, P-selectin or E-selectin affinity columns equilibrated in a buffer consisting of 20 mM Hepes, 125 mM NaCl, 2 mM $CaCl_2$, 2 mM $MgCl_2$, pH 7.45 (Koenig et al., supra, 1997). The column was washed and the bound PIM-Heparin eluted with the same buffer containing 2 mM EDTA (divalent cation-dependent component) in place of 2 mM $CaCl_2$ and 2 mM $MgCl_2$. The second elution was with 20 mM Hepes (pH 7.45), 110 mM NaCl, 20 mM EDTA (divalent cation-independent component, EDTA acting as a polycarboxylate) and the fractions were collected as described above.

Using the L-selectin affinity column, 10% of the added PIM-heparin ran through, 58% of the heparin that bound to the column was eluted with 2 mM EDTA and the remaining 32% was eluted with 20 mM EDTA (FIG. 4B). In contrast, for the P-selectin column, 21% of the material ran through, very little was eluted with 2 mM EDTA, and the 79% that remained bound to the column required repeated washing with 20 mM EDTA for elution (FIG. 4C). For the E-selectin column, 100% of the PIM-heparin ran through (FIG. 4A).

These results demonstrate that the binding of PIM-heparin to the selectins is similar to that of the HS chains obtained from endothelial cells, except that a fraction of PIM-heparin remained bound to L-selectin after elution with 2 mM EDTA.

B. Calcium Dependence of Heparin Binding to L-selectin and to P-selectin

The calcium dependence of PIM-heparin binding to the L-selectin and P-selectin columns was determined as described above for endothelial HS chains. Aliquots of $^3H$-labeled PIM-Heparin were applied to an L-selectin and P-selectin affinity column in a magnesium/EGTA buffer having a residual free calcium concentration of 774 μM. The columns were washed, eluted and the fractions were collected as described above.

L-selectin and P-selectin binding by PIM-heparin was similar to the endothelial HS chains (FIG. 5). For the L-selectin column, 100% ran through; for the P-selectin column, 55% ran through, 3% eluted with 2 mM EDTA, and 42% eluted with 20 mM EDTA. Thus, binding to L-selectin was abolished in Mg++/EGTA buffers, in which calcium was present in negligible amounts. The fraction bound to P-selectin was lower (45% vs. 79%) than that detected under calcium-replete conditions indicating a partial calcium dependency of the initial binding (compare FIG. 5 with FIG. 4). The fraction that did bind in the absence of calcium required 20 mM EDTA for elution (FIG. 5B).

These results demonstrate that calcium assists the initial binding of some PIM-heparin fragments to P-selectin. However, once bound, calcium is not required to maintain the interaction of the heparin chains with P-selectin.

EXAMPLE III

Binding and Characterization of Size-Defined Heparin Fragments

This example shows that L-selectin and P-selectin exhibit differential preferences in their binding towards heparin fragments.

A. Binding of Size-fractionated Heparin Fragments to the Selectin Columns

The binding of sized fragments of heparin to L-selectin and P-selectin was analyzed. Size-fragmented mixtures of PIM-heparin were prepared as previously described (Pervin et al., supra, 1995), labeled by reduction with $NaB(^3H)_4$ and purified as described above. Aliquots of the labeled PIM-heparin fragments were loaded onto the L-selectin and P-selectin affinity columns, washed, and the bound ligand eluted and fractions collected as described above. Again, L-selectin binding was eluted by 2 mM EDTA, whereas most of the binding to P-selectin required 20 mM EDTA for elution, although a small portion was eluted with 2 mM EDTA (see Table 4).

Figure 6A:
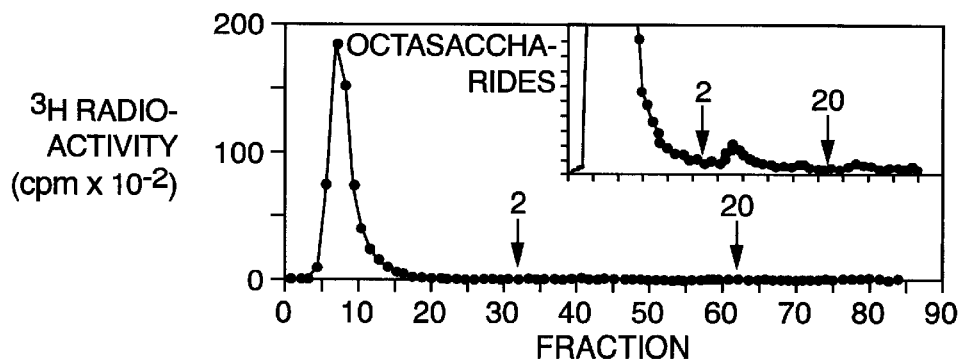
FIGS. 6A–6D show the size dependence of porcine mucosal heparin fragments in binding to an L-selectin affinity column.
Figure 6B:
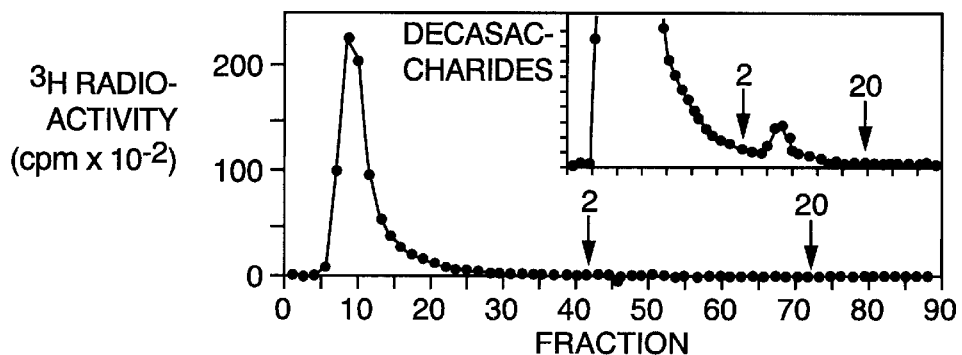
Figure 6C:
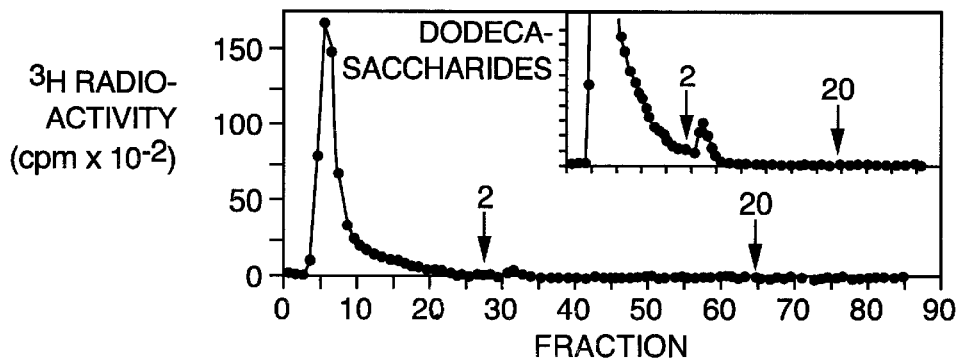
Figure 6D:
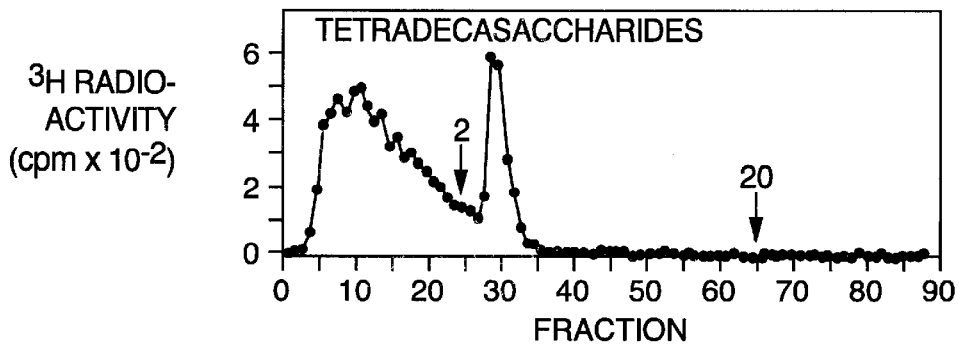
Figure 7A:
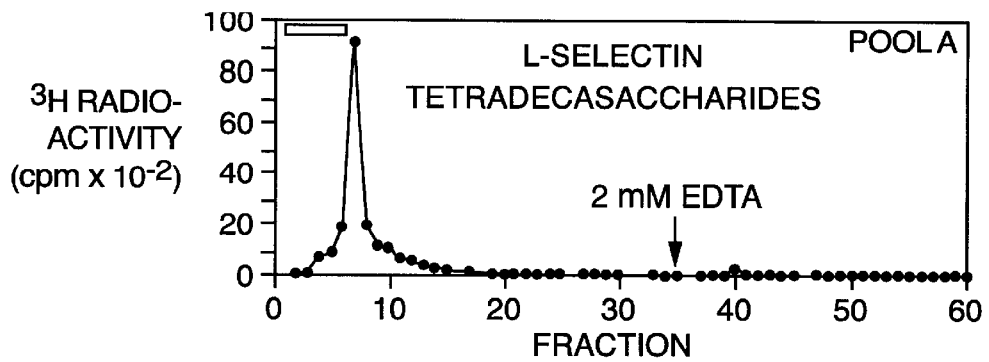
FIGS. 7A–7D show the results of rechromatographing PIM-heparin tetradecasaccharides on an L-selectin affinity column.
Figure 7B:
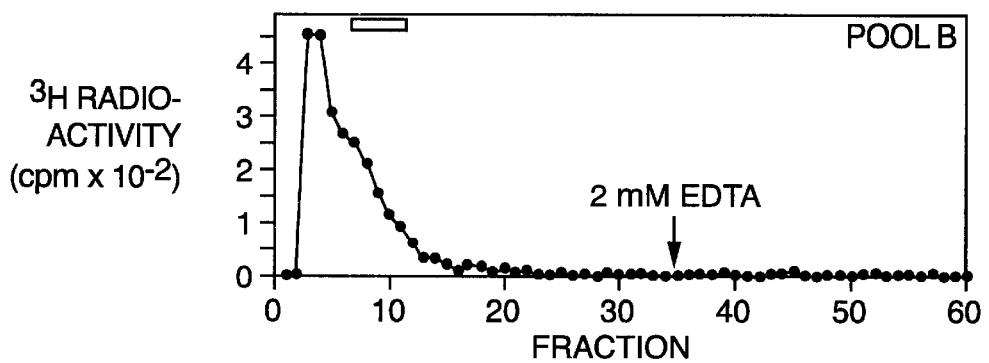
Figure 7C:
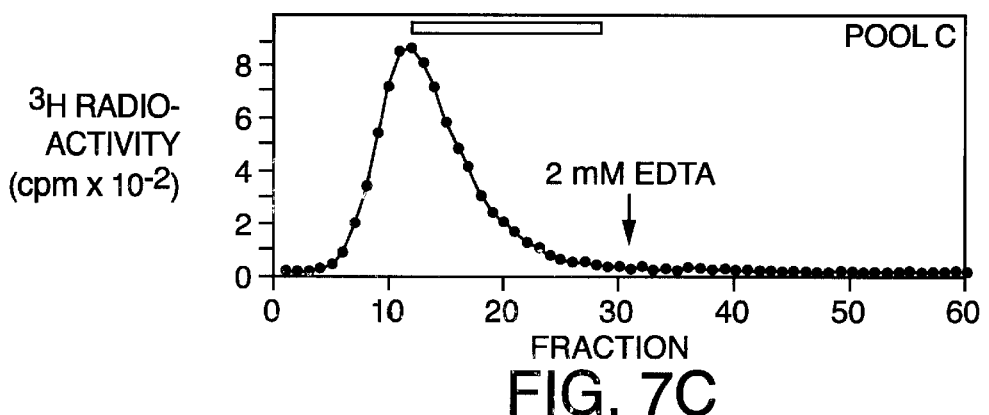
Figure 7D:
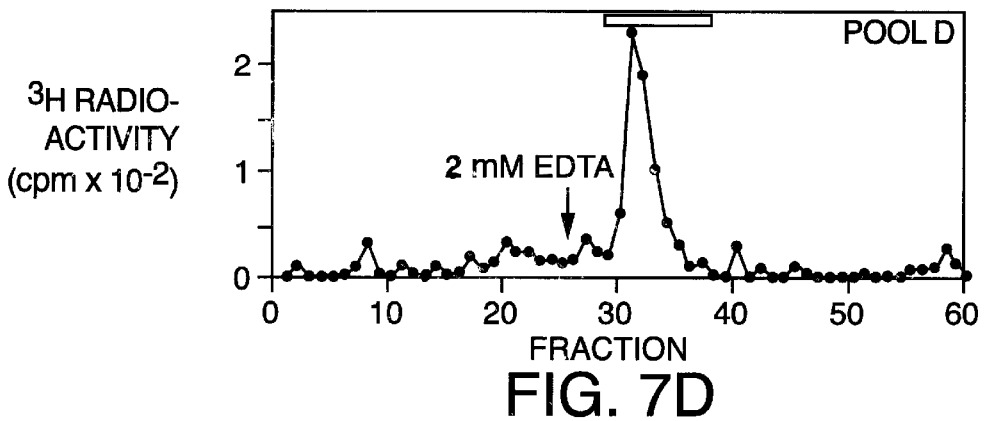

The results shown in FIG. 6 and Table 2 indicate that the binding of these ($^3H$)-heparin fragments to L-selectin and P-selectin is size dependent; substantial binding of tetradecasaccharides was observed (FIG. 6D). Under the conditions of affinity column chromatography used here, binding constants in the low $\mu M$ range are expected to be required for detection of binding. Consistent with this prediction, the tetradecasaccharides have $IC_{50}$ values in the low uM range for inhibition of L-selectin and P-selectin binding to $SLe^x$ (Table 3). Thus, the tetradecasaccharide mixture has $IC_{50}$ values that are about 6-fold to 10-fold greater than those reported for $SLe^x$ itself (tetradecasaccharides: 82 $\mu M$ and 54 $\mu M$ for P-selectin and L-selectin, respectively; and $SLe^x$: 520 $\mu M$ and 600 $\mu M$ for P-selection and L-selectin, respectively)o. Studies with $Mg^{++}$/EGTA buffers confirmed the calcium requirement for L-selectin binding, indicating that the divalent cation dependence of this interaction was similar to that of bulk heparin and of the endothelial HS chains.

The fractionated ($^3H$)-tetradecasaccharide heparin fragments were reapplied t o the L-select in and P-selectin columns to determine the reproducibility of the above results. In addition, cross-binding studies were performed to identify differences in the tetradecasaccharides that bound to L-selectin and P-selectin. ($^3H$)-tetradecasaccharides (approximately 500,000 cpm) were loaded onto L-selectin and P-selectin columns and the fractions collected as described above (only 0.5% of each fraction was monitored). Run-through and eluted fractions were desalted using a CENTRICON unit (Amicon, Beverly Mass.) and the isolated pools were stored in 250 $\mu l$ $H_2O$ at 4° C. Recoveries ranged from 50–99%.

For L-selectin, the pools were unbound (Pool A), slightly retarded (Pool B), retarded (Pool C) or eluted with EDTA (Pool D). For rebinding experiments, the pools were reapplied (2500 cpm) to the same column. For cross-binding experiments, ($^3H$)-tetradecasaccharides (2500 cpm) that bound to L-selectin were loaded onto the P-selectin column and the ($^3H$)-tetradecasaccharides (2500 cpm) that bound to P-selectin were loaded onto the L-selectin column. The columns were washed, eluted and the fractions were collected as previously described.

Rebinding of the pooled tetradecasaccharide fractions to L-selectin and P-selectin indicated that the binding profiles were reproducible (FIG. 7 and Table 4). In addition, 100% of the tetradecasaccharides that bound to L-selectin bound to P-selectin; these tetradecasaccharides were eluted with 20 mM EDTA (Table 4). Only a subfraction of the tetradecasaccharides that bound P-selectin also bound to L-selectin: 22% of the 2 mM EDTA-eluted and 51% of the 20 mM EDTA elutedmaterial. Of the fraction that did not bind to L-selectin, 12% rebound to P-selectin and eluted from the column only with 20 mM EDTA.

These findings indicate that, while L-selectin and P-selectin both exhibit some selectivity in recognizing heparin tetradecasaccharides, P-selectin has a more permissive range of recognition.

B. Analysis of the Structural Features of the Tetradecasaccharides that Determine Binding Behavior to P-selectin and L-selectin The structural differences that account for differential binding was investigated by determining the type of tetradecasaccharides that bound to L-selectin and P-selectin. Aliquots (2000 cpm) of the pooled fractions isolated from the L-selectin and P-selectin columns were subjected to cleavage either with specific heparin lyases (I, II and III) as previously described (Lohse and Linhardt, supra, 1992; Desai et al., supra, 1993; Jandik et al., supra, 1994; Linhardt, supra, 1996) or by nitrous acid treatment at pH 1.5 or pH 4.0 (Conrad, supra, 1996). These treatments result in the cleavage of heparin chains, the type of which depends upon specific structural features or modifications of the heparin molecule.

Heparin lyase I (0.1–0.05 units) was used to digest (H)-tetradecasaccharide, and 0.05 units were used to digest each of the pools at 30° C. for 8.5 hours in sodium phosphate/NaCl buffer, pH 7.1. Heparin lyase II (0.1 units) was used to digest all samples for 8 hours at 35° C. in sodium phosphate, buffer, pH 7.1. Heparin lyase III (0.2 units) was used to digest all samples for 11 hours at 35° C. in sodium phosphate buffer, pH 7.6. All digestions went to completion and were stopped by boiling for 5 minutes; samples were stored at −20° C.

Nitrous acid (HONO) degradation was performed by adding 100 u L of either the pH 1.5 or pH 4.0 HONO reagent to tubes containing the ($^3H$)-tetradecasaccharide or each pooled fraction. The reaction proceeded for 10 minutes at room temperature, then was quenched with either 15 $\mu l$ of 1 M $Na_2CO_3$ for the pH 4.0 reaction or 35 $\mu l$ of 1 M $Na_2CO_3$ for the pH 1.5 reaction to obtain a final pH of 7.5. pH controls for each reaction were used for every experiment and consisted of replacing the sodium nitrite with sodium acetate for the pH 4.0 reaction, and barium nitrite with barium acetate for the pH 1.5 reaction. Samples were stored at −20° C. until FPLC (forward phase liquid chromatography) analysis.

The size of the treated fractions were determined by FPLC using a SUPERDEX 75 HR 10/30 column (Pharmacia, Alameda Calif.). The ($^3H$)-tetradecasaccharide starting mixture, and the L-selectin and P-selectin binding and nonbinding ($^3H$)-tetradecasaccharide-pools were analyzed in parallel. The column was run isocratically in the same buffer used for the selectin-Rg-PAS columns (20 mM Hepes (pH 7.45), 125 mM NaCl, 2 mM $MgCl_2$, 2 mm $CaCl_2$). An FPLC system (Pharmacia, P-LKB-Pump P-500; P-LKB-Controller LCC-500 Plus; LKB-Frac 100) was used to elute the column at 1.0 ml/minute flow rate and collect 0.25 minute fractions after 6 min from the beginning of the run to 21 min resulting in 60 fractions per run being collected. The fractions were collected in scintillation vials and the radioactivity determined. The elution profile of this column was highly reproducible from run to run, as determined by addition of blue dextran (void column) and PIM-heparin sized mixtures ranging from disaccharides to tetradecasaccharides, which were radiolabeled with NaB ($^3$H)$_4$ as described above. 50 µl of 1% blue dextran was added to every sample prior to loading onto the SUPERDEX 75 FPLC column to confirm run to run reproducibility.

L-selectin binding fragments were sensitive to Heparin Lyase I and HONO pH 1.5 and, therefore, the fragments included the more heavily sulfated and epimerized regions. The sensitivity to HONO, pH 4.0, treatment indicates that the L-selectin binding heparin tetradecasaccharide chains are enriched in the small amounts of free amino groups present in the mixture. The P-selectin binding component includes this fraction, as well as a fraction sensitive to Heparin Lyase III digestion which indicates the presence of less heavily modified tetradecasaccharide chains.

EXAMPLE IV

Heparin Inhibits L-Selectin and P-Selectin Binding

This example shows that pharmaceutical formulations of heparin can inhibit L-selectin and P-selectin binding.

A. Heparin Inhibits L-selectin and P-selectin Binding to SLe$^x$

The inhibitory properties of clinically formulated pharmaceutical heparin preparations were studied using ELISA inhibition assays.

ELISA inhibition assays were performed as previously reported (O'Connell et al., *Proc. Natl. Acad. Sci. USA* 93:5883–5887 (1996); Koenig et al., supra, 1997). Sterile 96 well ELISA plates were coated with 200 ng of polyacrylamide-SLe$^x$ (Glycotech; Rockville Md.) by overnight incubation at 40° C. in 100 µl of 50 mM sodium carbonate/bicarbonate buffer, pH 9.5. Plates were blocked for at least 2 hours at 4° C. with 200 µl of 20 mM Hepes, 125 mM NaCl, 2 mM CaCl$_2$, 2 mM MgCl$_2$, 1% protease-free BSA, pH 7.45 (osmolarity 290 milliosmoles) per well. During the blocking step, the selectin-Rg chimeras were separately preincubated at 4° C. with a peroxidase-conjugated goat anti-human IgG secondary antibody (Jackson Immunoresearch Laboratories, Inc.; West Grove Pa.) in assay buffer for approximately 1 hour.

Final selectin-Rg concentration was 20 nM, and the secondary antibody dilution was 1:1000. Potential binding inhibitors were serially diluted in assay buffer at twice the final required concentration. The selectin-Rg/secondary antibody stock was aliquoted into tubes containing an equivalent volume of inhibitor solution; buffer, alone, for the positive control; or buffer with 10 mM Na$_2$EDTA, pH 7.5, for the negative control (final concentration 5 mM EDTA).

These tubes were preincubated at 4° C. for 30 minutes, then added to ELISA plates, in duplicates, to a well volume of 100 µl. After 4 hours at 4° C., the plates were washed three times with 200 µl per well of assay buffer at 4° C., followed by development with 150 µl per well of OLD solution (0.002 mg o-phenylenediamine dyhydrochloride (OPD)/ml in 50 mM sodium citrate, 50 mM disodium phosphate buffer, 1 µl/ml 30% H$_2$O$_2$, pH 5.2) at room temperature. Each well was sequentially quenched with 40 µl of 4 M H$_2$SO$_4$ after a fixed amount of time. The absorbance at 492 nM was determined using SOFTMAX software and a microplate reader (Molecular Devices Inc., Menlo Park Calif.). Prior to curve fitting, the absorbance values were converted into percentages for comparative purposes using the formula: ({(average of duplicates)–(negative control)}/{(positive control)–(negative control)})×100) using the SOFTMAX software.

Two separate lots of pharmaceutical unfractionated heparin significantly inhibited L-selectin and P-selectin, but not E-selectin binding to immobilized SLe$^x$ (FIG. 8 and Table 5). The concentrations required were less than the recommended therapeutic range for anticoagulation; IC$_{50}$ values of 0.07–0.08 units/ml and 0.01–0.02 units/ml towards SLe$^x$-binding of L-selectin and P-selectin, respectively (Table 5). In addition, two different types of clinical grade LMW heparins, FRAGMIN and LOVENOX, gave IC$_{50}$ values of 0.7–2.0 units/ml and 0.8–1.5 units/ml for inhibition of L-selectin and 1.5–2.0 units/ml and 0.8–1.0 units/ml for inhibition of P-selectin binding, respectively, which were at or higher than the recommended therapeutic levels (see FIG. 8 and Table 5).

B. Heparin Inhibits L-selectin and P-selectin Binding to HL-60 Cells

The inhibitory properties of pharmaceutical heparin samples also were studied using HL-60 cell attachment assays. HL-60, a human promyelocytic leukemia cell line (ATCC; CCL 240)), was grown in RPMI 1640 media supplemented with 20% FBS (1% Pen-Strep/0.2% gentamycin) and used at or before 8 passages. The binding inhibition studies were performed by labeling HL-60 cells with ($^3$H)-thymidine (1 µCi/ml media) for two days. After labeling, the cells, at a density of 2×10$^6$ cells/ml or less, were collected by centrifugation, washed three times with 20 ml of media, resuspended and the number of cells (1×10$^4$ to 1×10$^5$ cells/well) and radioactivity were determined (0.3–1.7 cpm/cell). 1 pmole per well of L-selectin-Rg and P-selectin-Rg immobilized on 24 well tissue culture plates in 250 µl of 50 mM sodium carbonate/bicarbonate buffer, pH 9.5, for 8 to 12 hours at 4° C. were blocked for 2 hours at 4° C. with 500 µl per well of 20 mM Hepes, 125 mM NaCl, 2 mM CaCl$_2$, 2 mM MgCl$_2$, and 1% protease-free BSA, pH 7.45.

Serial dilutions of unfractionated and LMW heparins were prepared in duplicate as described above and aliquots of ($^3$H)-HL-60 cells added for a final volume of 250 µl per well. Positive control wells with ($^3$H)-HL-60 cells alone and negative controls including 20 mM EDTA were analyzed in triplicate. After incubation for 3–4 hours at 4° C. with gentle rotation, the wells were washed 3 times with 500 µl cold assay buffer lacking BSA. Bound cells were solubilized at room temperature for 10 minutes in 1% Triton X-100 and the lysate monitored for radioactivity. IC$_{50}$ values are expressed as a percentage of the positive control and calculated as described above for the ELISA inhibition experiments (Table 5).

Unfractionated heparin inhibits the interaction of HL-60 with L-selectin and P-selectin (FIG. 9). The IC$_{50}$ values calculated are 0.02–0.03 units/ml for L-selectin and 0.003–0.01 units/ml for P-selectin (Table 5). These values are approximately 12-fold and 50-fold lower than the recommended therapeutic range for heparin anticoagulant therapy. These results indicate that levels of heparin less than those used in anticoagulation therapy are effective at inhibiting L-selectin and P-selectin binding. The results also indicate that the two low molecular weight heparins (FRAGMIN and LOVENOX) are much poorer inhibitors of L-selectin and P-selectin binding to sialylated ligands, including the Hl-60 ligand PSGL-1 (FIG. 9 and Table 5).

Although the invention has been described with reference to the examples provided above, it should be understood that various modifications can be made without departing from the spirit of the invention.

18. Albeida, S. M., C. W. Smith, and P. A. Ward. 1994. Adhesion molecules and inflammatory injury. FASEB J. 8:504–512.
25. Tedder, T. F., D. A. Steeber, A. Chen, and P. Engel. 1995. The selectins: Vascular adhesion molecules. FASEB J. 9:866–873.
57. Ridings, P. C., S. Holloway, G. L. Bloomfield, M. L. Phillips, B. J. Fisher, C. R. Blocher, H. J. Sugerman, and A. A. Fowler,III. 1997. Protective role of synthetic sialylated oligosaccharide in sepsis-induced acute lung injury. J. Appl. Physiol. 82:644–651.
58. Mengelers, H. J. J., T. Maikoe, B. Hooibrink, T. W. Kuypers. J. Kreukniet, J.-W. J. Lammers. and L. Koenderman. 1993. Down modulation of L-Selectin expression on cosinophils recovered from bronchoalveolar lavage fluid after allergen provocation. Clin. Exp. Allergy 23:196–204.
59. Georas, S. N., M. C. Liu, W. Newman, L. D. Beall, B. A. Stealey, and B, S. Bochner. 1992. Altered adhesion molecule expression and endothelial cell activation accompany the recruitment of human granulocytes to the lung after segmental antigen challenge. Am. J. Respir. Cell Mol. Biol. 7:261–269.
60. Mulligan, M. S., S. R. Watson, C. Fennie, and P. A. Ward. 1993. Protective effects of selectin chimeras in neutrophil-mediated lung injury. J. Immunol. 151:6410–6417.
61. Mulligan, M. S., M. Miyasaka, T. Tamatani, M. L. Jones, and P. A. Ward, 1994. Requirements for L-selectin in neutrophil-mediated lung injury in rats. J. Immunol. 152:832–840.
62. Doyle, N. A., S. D. Bhagwan, B. B. Meek, G. J. Kutkoski, D. A. Steeber, T. F. Tedder, and C. M. Doerschuk. 1997. Neutrophil margination, sequestration, and emigration in the lungs of L-selectin-deficient mice. J. Clin. Invest. 99:526–533.
63. Mulligan, M. S., J. C. Paulson, S. De Frees, Z.-L. Zheng, J. B. Lowe, and P. A. Ward. 1993. Protective effects of oligosaccharides in P-selectin-dependent lung injury. Nature 364:149–151.
64. Mulligan, M. S., M. Miyasaka, Y. Suzuki, H. Kawashima, M. Iizuka. A. Hasegawa, M. Kiso, R. L. Warner, P. A. Ward, and T. Suzuki. 1995. Anti-inflammatory effects of sulfatides in selectin-dependent acute lung injury [published erratum appears in Int Immunol 1995 October;7(10):1699]. Int. Immunol. 7:1107–1113.
65. Burns, A. R. and C. M. Doerschuk. 1994. Quantitation of L-selectin and CD 18 expression on rabbit neutrophils during CD 18-independent and CD 18dependent emigration in the lung. J. Immunol. 153:3177–3188.
66. Mizgerd, J. P., B. B. Meek, G. J. Kutkoski, D. C. Bullard, A. L. Beaudet, and C. M. Doerschuk. 1996. Selectins and neutrophil traffic: Margination and *Streptococcus pneumoniae*-induced emigration in murine lungs. J. Exp. Med. 184:639645.
67. Seekamp, A., G. O. Till, M. S. Mulligan, S. C. Paulson, D. C. Anderson, M. Miyasaka, and P. A. Ward. 1994. Role of selectins in local and remote tissue injury following ischemia and reperfusion. Am. J. Pathol. 144:592–598.
68. Moore, T. M., P. Khimenko, W. K Adkins, M. Miyasaka, and A. E. Taylor. 1995. Adhesion molecules contrbute to ischemia and reperfusion-induced injury in the isolated rat lung. J. Appl. Physiol. 78:2245–2252.
69. Ridings, P. C., A. C. J. Windsor, M. A. Jutila, C. R. Blocher, B. J. Fisher, M. M. Sholley, H. J. Sugerman, and A. A. Fowler,III. 1995. A dual-binding antibody to E- and L-selectin attenuates sepsis-induced lung injury. Am. J. Respir. Crit. Care Med. 152:247–253.
70 Tedder. T. F., D. A. Steeber, and P. Pizcueta. 1995. L-selectin-deficient mice have impaired leukocyte recruitment into inflammatory sites. J. Exp. Med. 181:2259–2264.
71. Catalina, M. D., M. C. Carroll, H. Arizpe, A. Takashima, P. Estess, and M. H. Siegelman. 1996. The route of antigen entry determines the requirement for L-selectin during immune responses. J. Exp. Med. 184:2341–2351.
72. Narasinga Rao, B. N., M. B. Anderson J. H. Musser, J. H. Gilbert, M. E. Schaefer, C. Foxall, and B K Brandley 1994 Sralyl Lewis X mimics derived from a pharmacophore search are selectin inhibitors with anti-inflammatory activity. J. Biol. Chem. 269:19663–19666.
73. Elbim, C., M. H. Prevor, F. Bouscarat, E. Franzini, S. Chollet-Martin, J: Hakim, and M. A. Gougerot-Pocidalo. 1994. Polymorphonuclear neutrophils from human immnunodeficiency virus-infected patients show enhanced activation, diminished fMLP-induced L-selectin shedding, and an impaired oxidative burst after cytokine priming. Blood 84:2759–2766.
74. Xu, J. C., I. S. Grewal, G. P. Geba, and R. A. Flavell. 1996. Impaired primary T cell responses in L-selectin-deficient mice. J. Exp. Med. 183:589–598.
75. Zhang, J. G., L. Morgan, and G. P. Spickett. 1996. L-selectin in patients with common variable immunodeficiency (CVID): A comparative study with normal individuals. Clin. Exp. Immunol. 104:275–279.
76. Kawaishi, K., A. Kimura, O. Katoh, A. Sasaki, N. Oguma, A. Ihara, and Y. Satow. 1996. Decreased L-selectin expression in CD34-positive cells from patients with chronic myelocytic leukaemia. Br. J. Haematol. 93:367–374.
77. Aziz, K. E., P. J. McCluskey, and D. Wakefield. 1996. Expression of selectins (CD62 E,L,P) and cellular adhesion molecules in primary Sjogren's syndrome: Questions to immunoregulation. Clin. Immunol. Immunopathol. 80:55–66.
78. Munro, J. M., D. M. Briscoe, and T. F. Tedder. 1996. Differential regulation of leucocyte L-selectin (CD62L) expression in normal lymphoid and inflamed extralymphoid tissues. J. Clin. Pathol. 49:721–727.
79. Steeber, D. A., N. E. Green, S. Sato, and T. F. Tedder. 1996. Humoral immune responses in L-selectin-deficient mice. J. immunol. 157:4899–4907.
80. Sweki, A., A.-S. Cordey, N. Monai, J.-C. De Flaugerues, M. Schapira, and O. Spertini. 1995. Cleaved L-selectin concentrations in meningeal leukaemia. Lancet 345:286–289.
81. Hänninen, A., C. Taylor, P. R. Streeter, L. S. Stark, J. M. Sarte, J. A. Shizuru, O. Simell, and S. A. Michie. 1993. Vascular addressins are induced on islet vessels during insulitis in nonobese diabetic mice and are involved in lymphoid cell binding to islet endothelium. J. Clin. Invest. 92:2509–2515.
82. Yang, X.-D., N. Karin, R. Tisch, L. Steinman, and H. O. McDevitt. 1993. Inhibition of insulitis and prevention of diabetes in nonobese diabetic mice by blocking L-selectin and very late antigen 4 adhesion receptors. Proc. Natl. Acad. Sci. USA 90:10494–10498.
83. Lepault, F., M.-C. Gagnerault, C. Faveeuw, H. Bazin, and C. Boitard. 1995. Lack of L-selectin expression by cells transferring diabetes in NOD mice: Insights into the mechanisms involved in diabetes prevention by Mel-14 antibody treatment, Eur. J. Immunol, 25:1502–1507.
84. Hosaka, S., M. R. Shah, R. M. Pope, and A. E. Koch. 1996. Soluble forms of P-selectin and intercellular adhe- 85. Blann, A. D., P. A. Sanders, A. Herrick, and M. I. V. Jayson. 1996. Soluble L-selectin in the connective tissue diseases. *Br. J. Haematol.* 95:192–194.
86. Inagaki, H., K. Suzuki, K. Nomoto, and Y. Yoshikai. 1996. Increased susceptibility to primary infection with *Listeria monocytogenes* in germfree mice may be due to lack of accumulation of L-selectin$^+$ CD44$^+$ T cells in sites of inflammation. *Infect. Immun.* 64:3280–3287.
87. Kajihara, J., Y. Guoji, K. Kato, and Y. Suzuki. 1995. Sulfatide, a specific sugar ligand for L-selectin, blocks $CCl_4$-induced liver inflammation in rats. *Biosci. Biotechnol. Biochem.* 59:155–157.
88. Wada, Y., T. Saito, N. Matsuda, H. Ohmoto, K. Yoshino, M. Ohashi, H. Kondo, H. Ishida, M. Kiso, and A. Hasegawa. 1996. Studies on selectin blockers .2. Novel selectin blocker as potential therapeutics for inflammatory disorders. *J. Med. Chem.* 39:2055–2059.
89. Mihelcic, D., B. Schleiffenbaum, T. F. Tedder, S. R. Sharar, J. M. Harlan, and R. K Winn. 1994. Inhibition of leukocyte L-selectin function with a monoclonal antibody attenuates reperfusion injury to the rabbit ear. *Blood* 84:2322–2328.
90. Han, K. T., S. R. Sharar, M. L. Phillips, J. M. Harlan, and R. K. Winn. 1995. Sialyl Lewis$^x$ oligosaccharide reduces ischemia-reperfusion injury in the rabbit ear. *J. Immunol.* 155:401 1–4015.
91. McGill, S. N., N. A. Ahmed, F. Hu, R. P. Michel, and N. V. Christou. 1996. Shedding of L-selectin as a mechanism for reduced polymorphonuclear neutrophil exudation in patients with the systemic inflammatory response syndrome. *Arch. Surg.* 131:1141–1146.
92. Ahmed, N. A. and N. V. Christou. 1996. Decreased neutrophil L-selectin expression in patients with systemic inflammatory response syndrome. *Clin Invest. Med.* 19:427–434.
93. Cecconi, O., R. M. Nelson, W. G. Roberts, K. Hanasaki, G. Mannori, C. Schulz, T. R. Ulich, A. Aruffo, and M. P Bevilacqua. 1994. Inositol polyanions. Noncarbohydrate inhibitors of L- and P-selectin that block inflammation. *J. Biol. Chem.* 269:15060–15066.
94. Briggs. J. B., Y. Oda, J. H. Gilbert, M. E. Schaefer, and B. A. Macher. 1995. Peptides inhibit selectin-mediated cell adhesion in vitro, and neutrophil influx into inflammatory sites in vivo. *Glycobiology* 5:583–588.
95. Mannori, G., P. Crottet. O. Cecconi, K. Hanasaki, A. Aruffo, R. M. Nelson, A. Varki, and M. P. Bevilacqua. 1995. Differential colon cancer cell adhesion to E-, P-, and L-selectin: Role of mucin type glycoproteins. *Cancer Res.* 55:4425–4431.
96. Kawabata, K., Y. Nagake, K. Shikata, H. Makino, and Z. Ota. 1996. The changes of Mac-1 and L-selectin expression on granulocytes and soluble L-selectin level during hemodialysis. *Nephron* 73:573–579.
97. Rabb, H., G. Ramirez, S. R. Saba, D. Reynolds, J. C. Xu, R. Flavell, and S. Antonia. 1996. Renal ischemic-reperfusion injury in L-selectin-deficient mice. *Am. J. Physiol. Renal,Fluid Electrolyre Physiol.* 271:F408–F413.
98. Ley, K., G. Linnemann, M. Meinen, L. M. Stoolman, and P. Gaehtgens. 1993. Fucoidin, but not yeast polyphosphomannan PPME, inhibits leukocyte rolling in venules of the rat mesentery. *Blood* 81:177–185.
99. Kuijper, P. H. M., H. I. G. Torres, J. A. M. Van der Linden, J. W. I. Lammers, J. J. Sixma, L. Koenderman, and J. J. Zwaginga. 1996. Platelet-dependent primary hemostasis promotes selectin- and integrin-mediated neutrophil adhesion to damaged endothelium under flow conditions. *Blood* 87:3271–3281.
100. Buerke, M., A. S. Weyrich, Z. Zheng, F. C. A. Gaeta, M. J. Forrest, and A. M. Lefer. 1994. Sialyl Lewis$^x$-containing oligosaccharide attenuates myocardial reperfusion injury in cats. *J. Clin. Invest.* 93:1140–1148.
101. Miura, T., D. P. Nelson, M. L. Schermerhorn, T. Shin'oka, G. Zund, P. R. Hickey, E. J. Neufeld, and J. E. Mayer,Jr., 1996. Blockade of selectin-mediated leukocyte adhesion improves postischemic function in lamb hearts. *Ann. Thorac. Surg.* 62:1295–1300.
102. Flynn, D. M., A. I. Buda, P. R. Jeffords, and D. J. Lefer. 1996. Sialyl Lewis$^x$-containing carbohydrate reduces infarct size: Role of selectins in myocardial reperfusion injury. *Am. J. Physiol. Heart Circ. Physiol.* 271:H2086–H2096.
103. Ma, X., A. S. Weyrich, D. J. Lefer, M. Buerke, K. H. Albertine, T. K. Kishimoto, and A. M. Lefer. 1993. Monoclonal antibody to L-selectin attenuates neutrophil accumulation and protects ischemic reperfused cat myocardium. *Circulation* 88:649–658.
104. Buerke, M., A. S. Weyrich, T. Murohara, C. Queen, C. K. Klingbeil, M. S. Co, and A. M. Lefer. 1994. Humanized monoclonal antibody DREG-200 directed against L-selectin protects in feline myocardial reperfusion injury. *J. Pharmacol. Exp. Ther.* 271:134–142.
105. Lefer, A. M. 1995. Role of selectins in myocardial ischemia reperfusion injury. *Ann. Thorac Surg.* 60:773–777.
106. Haught, W. H., M. Mansour, R. Rothlein, T. K. Kishimoto, E. A. Mainolfi, J. B. Hendricks, C. Hendricks, and J. L. Mehta 1996. Alterations in circulating intercellular adhesion molecule-1 and L-selectin: Further evidence for chronic inflammation in ischernic heart disease. *Am. Heart J.* 132:1–8.
107. Murohara, T., M. Buerke, and A. M. Lefer. 1994. Polymorphonuclear leukocyte-induced vasocontraction and endothelial dysfunction: Role of selectins. *Arterioscler. Thromb.* 14:1509–1519.
108. Ramamoorthy, C., S. R. Sharar, J. M. Harlan, T. F. Tedder, and R. K. Winn. 1996. Blocking L-selectin function attenuates reperfision injury following hemorrhagic shock in rabbits. *Am. J. Physiol. Heart Circ. Physiol.* 271:H1871–H1877.
109. Blann, A., J. Morris, and C. McCollum. 1996. Soluble L-selectin in peripheral arterial disease: Relationship with soluble E-selectin and soluble P-selectin. *Atherosclerosis* 126:227–231.
110. Turunen, J. P., M. L. Majuri, A. Seppo, S. Tiisala, T. Paavonen, M. Miyasaka, K. Lemström, L. Pentrilǎ, O. Renkonen. and R. Renkonen, 1995. De novo expression of endothelial sialyl Lewis$^a$ and sialyl Lewis$^x$ during cardiac transplant rejection: Superior capacity of a tetravalent sialyl Lewis$^x$ oligosaccharide in inhibiting L-selectin-dependent lymphocyte adhesion. *J. Exp. Med.* 182:1133–1141.
111. Bargatze, R. F., S. Kurk, G. Watts, T. K. Kishimoto, C. A Speer, and M. A. Jutila, 1994. In vivo and in vitro functional examination of a conserved epitope of L- and E-selectin crucial for leukocyte-endothelial cell interactions. *J. Immunol.* 152:5814–5825.
112. Granert, C. J. Raud, X. Xie, L. Lindquist, and L. Lindbom. 1994. Inhibition of leukocyte rolling with polysaccharide fucoidin prevents pleocytosis in experimental meningitis in the rabbit. *J. Clin. Invest.* 93:929–936.

113. Dopp, J. M., S. M. Breneman, and J. A. Olschowka. 1994. Expression of ICAM-1, VCAM-1, L-selectin, and leukosialin in the mouse central nervous system during the induction and remission stages of experimental allergic encephalomyclitis. *J. Neuroimmunol.* 5:129–144

114. Bührer, C., R. Harold, D. Stibenz, G. Henze, and M. Obladen. 1996. Cerebrospinal fluid soluble L-selectin (sCD62L) in meningoencephalitis. *Arch. Dis. Child.* 74:288–292.

115. Morikawa, E., S. M. Zhang, Y. Seko, T. Toyoda, and T. Kirino. 1996. Treatment of focal cerebral ischemia with synthetic oligopeptide corresponding to lectin domain of selectin. *Stroke* 27:951–955.

116. Mössner, R., K. Fassbender. J. Kühnen, A. Schwartz, and M. Hennerici. 1996. Circulating L-selectin in multiple sclerosis patients with active, gadolinium-enhancing brain plaques. *J. Neuroimmnunol.* 65:61–65.

117. Onrust, S. V., P. M. Hartl, S. D. Rosen, and D. Hanahan. 1996. Modulation of L-selectin ligand expression during an immune response accompanying tumorigenesis in transgenic mice. *J. Clin. Invest.* 97:54–64.

118. Wenisch, C., E. Presterl, W. Graninger, and S. Looarcesuwan. 1995. Circulating L-seletin is elevated in patients with *Plasmodium falciparum* malaria. *J. Infect. Dis.* 171:1078.

119. Rebuck, N., A. Gibson, and A. Finn. 1995. Neutrophil adhesion molecules in term and premature infants: Normal or enhanced leucocytc integrins but defective L-selectin expression and shedding. *Clin. Exp. Immunol.* 101:183–189.

120. Bührer, C., D. Stibenz, J. Graulich, U. Gernhold, E. C. Butcher, J. W. Dudenhausen, and M. Obladen. 1995. Soluble L-selectin (sCD62L) umbilical cord plasma levels increase with gestational age. *Pediatr. Res.* 38:336–341.

121. Wenisch, C., D. Myskiw, A. Gessi, and W. Graninger. 1995. Circulating selectins, intercellular adhesion molecule-1, and vascular cell adhesion molecule-1 in hyperthyroidism. *J. Clin. Endocrinol. Metab.* 80:2122–2126.

122. Mulligan, M. S., M. J. Polley, R. J. Bayer, M. F. Nunn, J. C. Paulson, and P. A. Ward. 1992. Neutrophildependent acute lung injury. Requirement for P-selectin (GMP-140). *J. Clin. Invest.* 90:1600–1607.

123. Carden, D. L., J. A. Young, and D. N. Granger. 1993. Pulmonary microvascular injury after intestinal ischemiareperfusion: Role of P-selectin. *J. Appl. Physiol.* 75:2529–2534.

124. Shenkar, R., A. J. Cohen, D. Vestweber, Y. E. Miller, R. Tuder, and E. Abraham. 1995. Hemorrhage and resuscitation alter the expression of ICAM-1 and P-selectin in mice. *Circ. Shock* 45:248–259.

125. Kushimoto, S., K. Okajima, M. Uchiba, K. Murakami, H. Okabe, and K., Takatsuki. 1996. Pulmonary vascular injury induced by hemorrhagic shock is mediated by P-selectin in rats. *Thromb. Res.* 82:97–106.

126. Doerschuk, C. M., W. M. Quinlan. N. A. Doyle, D. C. Bullard, D. Vestweber, M. L. Jones, F. Takei, P. A. Ward, and A. L. Beaudet. 1996. The role of P-selectin and ICAM-1 in acute lung injury as determined using blocking antibodies and mutant mice. *J. Immunol.* 157:4609–4614.

127. Sakamaki, F., A. Ishizaka, M. Handa, S. Fujishima, T. Urano, K. Sayarna, H. Nakamura, M. Kanazawa, T. Kawashiro, M. Katayama, and Y. Ikeda. 1995. Soluble form of P-selectin in plasma is elevated in acute lung injury. *Am. J. Respir. Crit. Care Med.* 151:1821–1826.

128. De Sanctis, G. T., W. W. Wolyniec, F. H. Y. Green, S. X. Qin, A. P. Jiao, P. W. Finn, T. Noonan, A. A. Joetham, E. Gelfand, C. M. Doerschuk, and J. M. Drazen. 1997. Reduction of allergic airway responses in P-selectindeficient mice. *J. Appl. Physiol.* 83:681–687.

129. Zeb, T., B. Piedboeuf, M. Gamache, C. Langston, and S. E. Welty. 1996. P-Selectin is upregulated early in the course of hyperoxic lung injury in mice. *Free Radic. Biol. Med.* 21:567–574.

130. Pottratz, S. T., T. D. Hall, W. M. Scribner, H. N. Jayaram, and V. Natarajan. 1996. P-selectin-mediated attachment of small cell lung carcinoma to endothelial cells. *Am. J. Physiol. Lung Cell. Mol. Physiol.* 271:L918–L923.

131. Ohkawara, Y., K. Yamauchi, N. Maruyama, H. Hoshi, I. Ohno, M. Honma, Y. Tanno, G. Tamara, K. Shirato, and H. Ohtani, 1995. In situ expression of the cell adhesion molecules in bronchial tissues from asthmetics with air flow limitation: in vivo evidence of VCAM-1/VLA-4 interaction in selective eosinophil infiltration. *Am. J. Respir. Cell Mol. Biol.* 12:4–12.

132. Henriques, G. M. O., J. M. Miotla, R. S. B. Cordeiro, B. A. Wolitzky, S. T. Woolley, and P. G. Hellewell. 1996. Selectins mediate eosinophil recruitment in vivo: A comparison with their role in neutrophil influx. *Blood* 87:5297–5304.

133. Mayadas, T. N. 1995. Gene knockout on P-selectin: Its biology and function. *Trends Cardiovasc. Med.* 5:149–157.

134. Simons, R. K., D. B. Hoyt, R. J. Winchell, R. M. Rose, and T. Holbrook. 1996. Elevated selectin levels after severe trauma: A marker for sepsis and organ failure and a potential target for immunomodulatory therapy. *J. Trauma Injury Infect. Crit. Care* 41:653–662.

135. Hansbrough, J. F., T. Wikström, M. Braide, M. Tenenhaus, O. H. Rennekampff, V. Kiessig, R. Zapata-Sirvent, and L. M. Bjursten. 1996. Effects of E-selectin and P-selectin blockade on neutrophil sequestration in tissues and neutrophil oxidative burst in burned rats. *Crit. Care Med.* 24:1366–1372.

136. Philips, M. L., B. R. Schwartz, A. Etzioni, R. Bayer, H. D. Ochs, J. C. Paulson, and J. M. Harlan. 1995. Neutrophil adhesion inleukocyte adhesion deficiency syndrome type 2. *J. Clin. Invest.* 96:2898–2906.

137. Bullard, D. C., E. J. Kunkel, H. Kubo, M. J. Hicks, I. Lorenzo, N. A. Doyle, C. M. Doerschuk, K. Ley, and A. L. Beaudet. 1996. Infectious susceptibility and severe deficiency of leukocyte rolling and recruitment in E-selectin and P-selectin double mutant mice. *J. Exp. Med.* 183:2329–2336.

138. Ohnishi, M., H. Koike, N. Kawamura, S. J. Tojo, M. Hayashi, and S. Morooka. 1996. Role of P-selectin in the early stage of the Anhus reaction. *Immunopharmacology* 34:161–170.

139. Austrup, F., D. Vestweber, E. Borges, M. Löhning, R. Bräuer, U. Hen, H. Renz, R. Hallmann, A. Scheffold, A. Radbruch, and A. Hamann. 1997. P- and E-selectin mediate recruitment of T-helper-1 but not T-helper-2 cells into inflamed tissues. *Nature* 385:81–83.

140. Borges, E., W. Tietz, M. Steegmaier, T. Moll, R. Hallmann, A. Hamann, and D. Vestweber. 1997. P-selectin glycoprotein ligand-1 (PSGL-1) on T helper 1 but not on T helper 2 cells binds to P-selectin and supports migration into inflamed skin. *J. Exp. Med.* 185:573–578.

141. Johnson, R. C., T. N. Mayadas, P. S. Frenette, R. E. Mebius, M. Subramaniam, A. Lacasce, R. O. Hynes, and D. D. Wagner. 1995. Blood cell dynamics in P-selectindeficient mice. *Blood* 86:1106–1114.

142. Bruserud, O., P. E. Akselen, J. Bergheim, and I. Nesthus. 1995. Serum concentrations of E-selectin, P-selectin, ICAM-1 and interleukin 6 in acute leukaemia patients with chemotherapy-induced leucopenia and bacterial infections. *Br. J. Haematol.* 91:394–402.

143. Frenette, P. S., T. N. Mayadas, H. Rayburn, R. O. Hynes, and D. D. Wagner. 1996. Susceptibility to infection and altered hematopoiesis in mice deficient in both P- and E-selectins. *Cell* 84:563–574.

144. Jilma, B., P. Fasching, C. Ruthner, A. Rumplmayr, S. Ruzicka, S. Kapiotis, O. F. Wagner, and H. G. Eichler. 1996. Elevated circulating P-selectin in insulin dependent diabetes mellitus. *Thromb. Haemost.* 76:328–332.

145. Salmi, M., P. Rajala, and S. Jalkanen. 1997. Homing of mucosal leukocytes to joints-Distinct endothelial ligands in synovium mediate leukocyte-subtype specific adhesion. *I. Clin. Invest.* 99:2165–2172.

146. Walter, U. M. and A. C. Issekutz. 1997. The role of E- and P-selectin in neutrophil and monocyte migration in adjuvant-induced arthritis in the rat. *Eur. J. Immunol.* 27:1498–1505.

147. Weiser, M. R., S. A. L. Gibbs, C. R. Valeri, D. Shepro, and H. B. Hechiman. 1996. Anti-selectin therapy modifies skeletal muscle ischemia and reperfusion injury. *Shock* 5:402–407.

148. Nolte, D., P. Schmid, U. Jäger, A. Botzlar, F. Roesken, R. Hecht, E. Uhl, K. Messmer. and D. Vestweber. 1994. Leuckocyte rolling in venules of striated muscle and skin is mediated by P-selectin. not by L-selectin. *Am. J. Physiol. Heart Circ. Physiol.* 267:H1637–H1642.

149. Garcia-Criado, F. J., L. H. Toledo-Pereyra, F. Lopez-Neblina, M. L. Phillips, A. Paez-Rollys, and K. Misawa. 1995. Role of P-selectin in total hepatic ischemia and reperfusion. *J. Am. Coll. Surgeons* 181:327–334.

150. Rubio Avilla, J., J. M. Palma-Vargas, J. T. Collins, R. Smejkal, J. McLaren, L. M. Phillips, and L. H. Toledo-Pereyia. 1997. Sialyl Lewis$^x$ analog improves liver function by decreasing neutrophil migration after hemorrhagic shock. *J. Trauma Injury Infect. Crit. Care* 43:313–318.

151 Silber, A. W. Newman, K. A. Reimann, E. Hendricks, D. Walsh, and D. J. Ringler. 1994. Kinetic expression of endothelial adhesion molecules and relationship to leukocyte recruitment in two cutaneous models of inflammation. *Lab. Invest.* 70:163–175.

152. Winn, R. K., D. Liggitt, N. B. Vedder, J. C. Paulson, and J. M. Harian. 1993. Anti-P-selectin monoclonal antibody attenuates reperfusion injury to the rabbit ear. *J. Clin. Invest.* 92:2042–2047.

153. Yamada, S., T. N. Mayadas, F. Yuan, D. D. Wagner, R. O. Hynes, R. J. Melder, and R. K. Jain. 1995. Rolling in P-selectin deficient mice is reduced but not eliminated in the dorsal skin. *Blood* 86:3487–3492.

154. Staite, N. D., J. M. Justen, L. M. Sly, A. L. Beaudet, and D. C. Bullard. 1996. Inhibition of delayed-type contact hypersensitivity in mice deficient in both E-selectin and P-selectin. *Blood* 88:2973–2979.

155. Subramaniam, M., S. Saffaripour, L. Van De Water, P. S. Frenette, T. N. Mayadas, R. O. Hynes, and D. D. Wagner. 1997. Role of endothelial selectins in wound repair. *Am. J. Pathol.* 150:1701–1709.

156. Kurose, I., T. Yamada, R. Wolf, and D. N. Granger. 1994. P-selectin-dependent leukocyte recruitment and intestinal mucosal injury induced by lactoferrin. *J. Leukocyte Biol.* 55:771–777.

157. Sun, X. M., R. A. Rozenfeld, X. W. Qu, W. Huang, F. Gonzalez-Crussi, and W. Hsueh. 1997. P-selectin-deficient mice are protected from PAF-induced shock, intestinal injury, and lethality. *Am. J. Physiol. Gastrointest. Liver Physiol.* 273:G56–G61.

158. Mayadas, T. N., R. C. Johnson, H. Rayburn, R. O. Hynes, and D. D. Wagner. 1993. Leukocyte rolling and extravasation are severely compromised in P selectin-deficient mice. *Cell* 74:541–554.

159. Kubes, P. and S. Kanwar. 1994. Histamine induces leukocyte rolling in post-capillary venules: A P-selectin-mediated event. *J. Immunol.* 152:3570–3577.

160. Kubes, P., I. Kurose, and D. N. Granger. 1994. NO donors prevent integrin-induced leukocyte adhesion but not P-selectin-dependent rolling in postischemic venules. *Am. J. Physiol. Heart Circ. Physiol.* 267:H931–H937.

161. Gibbs, S. A. L., M. R. Weiser, L. Kobzik, C. R. Valeri, D. Shepro, and H. B. Hechtman. 1996. P-selectin mediates intestinal ischemic injury by enhancing complement deposition. *Surgery* 119:652–656.

162. Schürmann, G. M., A. E. Bishop, P. Facer, M. Vecchio, J. C. W. Lee, D. S. Rampton, and J. M. Polak. 1995. Increased expression of cell adhesion molecule P-selectin in active inflammatory bowel disease. *Gut* 36:411–418.

163. Bullard, D. C., L. Qin, I. Lorenzo, W. M. Quinlin, N. A. Doyle, R. Bosse, D. Vestweber, C. M. Doerschuk, and A. L. Beaudet. 1995. P-selectin/ICAM-1 double mutant mice: Acute emigration of neutrophils into the peritoneum is completely absent but is normal into pulmonary alveoli. *J. Clin. Invest.* 95:1782–1788.

164. Panés, J., D. C Anderson, M. Miyasaka, and D. N. Granger. 1995. Role of leukocyce-endothelial cell adhesion in radiation-induced microvascular dysfunction in rats. *Gastroenterology* 108:1761–1769.

165. Suzuki, Y., H. Ohtani, T. Mizoi, S. Takeha, K. Shiiba, S. Matsuno, and H. Nagura. 1995. Cell adhesion molecule expression by vascular endothelial cells as an immune/inflammatory reaction in human colon carcinoma. *Jpn. J. Cancer Res.* 86:585–593.

166. Arndt, H., K. D. Palitzsch, D. C. Anderson, J. Rusche, M. B. Grisham, and D. N. Granger. 1995. Leucocyte-endothelial cell adhesion in a model of intestinal inflammation. *Gut* 37:374–379.

167. Tipping, P. G., X. R. Huang, M. C. Berndt, and S. R. Holdsworth. 1994. A role for P selectin in complement-independent neutrophil-mediated glomerular injury. *Kidney Int.* 46:79–88.

168. Tipping, P. G., X. R. Huang, M. C. Berndt, and S. R. Holdsworth. 1996. P-selectin directs T lymphocyte-mediated injury in delayed-type hypersensitivity responses: Studies in glomerulonephritis and cutaneous delayed-type hypersensitivity. *Eur. J. Immunol.* 26:454–460.

169. Takada, M., K. C. Nadeau, G. D. Shaw, K. A. Marquette, and N. L. tilney. 1997. The cytokine-adhesion molecule cascade in ischemia/reperfusion injury of the rat kidney—Inhibition by a soluble P-selectin ligand. *J. Clin. Invest.* 99:2682–2690.

170. Zizzi, H. C., G. B. Zibari, D. N. Granger, I. Singh, L. D. Cruz, F. Abreo, J. C. McDonald, and M. F. Brown. 1997 Quantification of P-selectin expression after renal ishemia and reperfusion *J. Pediatr. Surg.* 32:1010–1013.

171 Suematsu, M., H. Suzuki, T. Tamatini, Y. Iigou, F. A. DeLano, M. Miyasaka, M. J. Forrest, R. Kannagi, B. W. Zweifach, Y. Ishimura, and G. W. Schmid-Schönbein. 1995. Impairment of selectin-mediated leukocytc adhesion to venular endothelium in spontaneously hypenensive rats. *J. Clin. Invest.* 96:2009–2016.

172. Davenpeck, K. L., T. W. Gauthier, K. H. Albertine, and A. M. Lefer. 1994. Role of P-selectin in microvascular 173. Gauthier, T. W., K. L. Davenpeck, and A. M. Lefer. 1994. Nitric oxide attenuates leukocyte-endothelial interaction via P-selectin in splanchnic ischemia-reperfusion. *Am. J. Physiol. Gastrointest. Liver Physiol.* 267:G562–G568.

174. Weyrich, A. S., X. Ma, D. J. Lefer, K. H. Albertine, and A. M. Lefer. 1993. In vivo neutralization of P-selectin protects feline heart and endothelium in myocardial ischemia and reperfusion injury. *J. Clin. Invest.* 91:2620–2629.

175. Lefer, D. J., D. M. Flynn, M. L. Phillips, M. Ratcliffe, and A. J. Buda. 1994. A novel sialyl Lewis$^x$ analog attenuates neutrophil accumulation and myocardial necrosis after ischeria and reperfsion. *Circularion* 90:2390–2401.

176. Lefer, D. J., D. M. Flynn, and A. I. Buda. 1996. Effects of a monoclonal antibody directed against P-selectin after myocardial ischemia and reperfusion. *Am. J. Physiol. Heart Circ. Physiol.* 270:H88–H98.

177. Scalia, R., T. Murohara, J. A. Delyani, T. O. Nossuli, and A. M. Lefer. 1996. Myocardial protection by N,N,N-trimethylsphingosine in ischemia reperfusion injury is mediated by inhibition of P-selectin. *J. Leukocyte Biol.* 59:317–324.

178. Tojo, S. J., S. Yokota, H. Koike, J. Schultz, Y. Hamazume, E. Misugi, K. Yamada, M. Hayashi, J. C. Paulson, and S. Morooka. 1996. Reduction of rat myocardial ischemia and reperfusion injury by sialyl Lewis x oligosaccharide and anti-rat P-selectin antibodies. *Glycobiology* 6:463–469.

179. Lefer, D. J., D. M. Flynn, D. C. Anderson, and A. J. Buda 1996. Combined inhibition of P-selectin and ICAM-1 reduces myocardial injury following ischemia and reperfusion. *Am. J. Physiol. Heart Circ. Physiol.* 271:H2421–H2429.

180. Chignier, E., M. Parise, L. McGregor, C. Delabre, S. Faucompret, and J. McGregor. 1994. A P-selectin/CD62P monoclonal antibody (LYP-20), in tandem with flow cytometry, detects in vivo activated circulating rat platelets in severe vascular trauma *Thromb. Haemost.* 72:745–749.

181. Lehr, H.-A., A. M. Olofsson, T. E. Carew, P. Vajkoczy, U. H. Von Andrian, C. Hübner, M. C. Berndt, D. Steinberg, K. Messmer, and K. E. Arfors. 1994. P-selectin mediates the interaction of circulating leukocytes with platelets and microvascular endothelium in response to oxidized lipoprotein in vivo. *Lab. Invest.* 71:380–386.

182. Palabrica, T., R. Lobb, B. C. Furie, M. Aronovitz, C. Benjamin, Y.-M. Hsu. S. A. Sajer, and B. Furie. 1992. Leukocyte accumulation promoting fibrin deposition is mediated in vivo by P-selectin on adherent platelets. *Nature* 359:848–851.

183. Winn, R. K., J. C. Paulson, and J. M. Harlan. 1994. A monoclonal antibody to P-selectin ameliorates injury associated with hemorrhagic shock in rabbits. *Am. J. Physiol. Heart Circ. Physiol.* 267:H2391–H2397.

184. Toombs, C. F., C. L. DeGraaf, J. P. Martin, J. G. Geng, D. C. Anderson, and R. J. Shebuski. 1995. Pretreatment with a blocking monoclonal antibody to P-selectin accelerates pharmacological thrombolysis in a primate model of arterial thrombosis. *J. Pharmacol. Exp. Ther.* 275:941–949.

185. Fujise, K., B. M. Revelle, L. Stacy, E. L. Madison, E. T. H. Yeh, J. T. Willerson, and P. J. Beck. 1997. A tissue plasminogen activator/P-selectin fusion protein is an effective thrombolytic agent. *Circulation* 95:715–722.

186. Lip, G. Y. H., A. D. Blann, J. Zarifis, M. Beevers, P. L. Lip, and D. G. Beevers. 1995. Soluble adhesion molecule P-selectin and endothelial dysfunction in essential hypertension: Implications for atherogenesis? A preliminary report. *J. Hypertens.* 13:1674–1678.

187. Subramaniatn, M., P. S. Frenette, S. Saffaripour, R. C. Johnson, R. O. Hynes, and D. D. Wagner, 1996. Defects in hemostasis in P-selectin-deficient mice. *Blood* 84:1238–1242.

188. Mazurov, A. V., D. V. Vinogradov, S. G. Khaspekova, A. V. Krushinsky, L. V. Gerdeva, and S. A. Vasthev. 1996. Deficiency of P-selectin in a patient with grey platelet syndrome *Eur. J. Heamatol* 57:38–41.

189. Close, C., M. Seigneur, M. Renard, and A. Pruvost. 1996. Influence of hypoxia and hypoxiareoxygenation on endothelial P-selectin expression. *Haemostasis* 26 Suppl. 4:177–181.

190. Closse, C., M. Seigneur, M. Renard, A. Pruvost, P. Dumain, F. Belloc, and M. R. Boisseau. 1997. Influence of hypoxia and hypoxia-reoxygenation on endothelial P-selectin expression. *Thromb. Res.* 85:159–164.

191. Koskinen, P. K. and K. B. Lemström. 1997. Adhesion molecule P-selectin and vascular cell adhesion molecule-1 in enhanced heart allograft arteriosclerosis in the rat. *Circulation* 95:191–196.

192. Sakai, A., N. Kume, E. Nishi, K. Tanoue, M. Miyasaka, and T. Kita. 1997. P-selectin and vascular cell adhesion molecule-1 are focally expressed in aortas of hypercholesterolemic rabbits before intimal accumulation of macrophages and T lymphocytes. *Arterioscler. Thromb. Vasc. Biol.* 17:310–316.

193. Tenaglia, A. N., A. J. Buda, R. G. Wilkins, M. K. Barron, P. R. Jeffords, K. Vo, M. O. Jordan, B. A. Kusnick, and D. J. Lefer. 1997. Levels of expression of P-selectin, E-selectin, and intercellular adhesion molecule-1 in coronary atherectomy specimens from patients with stable and unstable angina pectoris. *Am. J. Cardiol.* 79:742–747.

194. Ikeda, H., Y. Takajo, K. Ichiki, T. Ueno, S. Maki, T. Noda, K. Sugi. and T. Imaizuma. 1995. Increased soluble form of P-selectin in patients with unstable angina. *Circulation* 92:1693–1696.

195. Kaikita, K., H. Ogawa, H. Yasue, T. Sakamoto, H. Suefuji, H. Sumida, and K. Okumura 1995. Soluble P-selectin is released into the coronary circulation after coronary spasm. *Circulation* 92:1726–1730.

196. Tang, T., P. S. Frenette, R. O. Hynes, D. D. Wagner, and T. N. Mayadas. 1996. Cytokine-induced meningitis is dramatically attenuated in mice deficient in endothelial selectins. *J. Clin. Invest.* 97:2485–2490.

197. Whitcup, S. M., A. T. Kozhich, M. Lobanoff, B. A. Wolitzky, and C. C. Chan. 1997. Blocking both E-selectin and P-selectin inhibits endotoxin-induced leukocyte infiltration into the eye. *Clin. Immunnol. Immunopathol.* 83:45–52.

198. Suzuki, H., B. W. Zweifach, M. J. Forrest, and G. W. Schmid-Schönbein. 1995. Modification of leukocyte adhesion in spontaneously hypertensive rats by adrenal corticosteroids. *J. Leukocyte Biol.* 57:20–26.

199. Fox, S. B., G. D. H. Turner, K. C. Gatter, and A. L. Harris. 1995. The increased expression of adhesion molecules ICAM-3, E- and P-selectins on breast cancer endothelium. *J. Pathol.* 177:369–376.

200. Borgström, P., G. K. Hughes, P. Hansell, B. A. Wolitzky, and P. Sriramarao. 1997. Leukocyte adhesion in angiogenic blood vessels—Role of E-selectin, P-selectin, and β2 integrin in lymphotoxin-mediated leukocyte recruitment in tumor microvessels. *J. Clin. Invest.* 99:2246–2253.

We claim:

1. A method of selectively inhibiting selectin mediated binding in a subject by administering an amount of heparin that does not produce substantial anticoagulant activity or undesireable bleeding, wherein said selectin mediated binding is selected from the group consisting of L-selectin mediated binding and P-selectin mediated binding.

2. The method of claim 1, wherein the amount of heparin administered results in a concentration of about 0.05 to 0.4 units of heparin/ml of plasma.

3. The method of claim 1, wherein the amount of heparin administered results in a concentration of about 0.05 to 0.2 units of heparin/ml of plasma.

4. The method of claim 1, wherein the amount of heparin administered results in a concentration of about 0.05 to 0.1 units of heparin/ml of plasma.

5. The method of claim 1, wherein P-selectin mediated binding is inhibited.

6. The method of claim 5, wherein the amount of heparin administered results in a concentration of about 0.005 to 0.05 units of heparin/ml of plasma.

7. The method of claim 5, wherein the amount of heparin administered results in a concentration of about 0.005 to 0.02 units of heparin/ml of plasma.

8. A method of inhibiting L-selectin mediated binding in a subject by administering an amount of heparin that does not produce substantial anticoagulant activity or undesirable bleeding.

9. The method of claim 8, wherein the amount of heparin administered results in a concentration of about 0.05 to 0.4 units of heparin/ml of plasma.

10. The method of claim 8, wherein the amount of heparin administered results in a concentration of about 0.05 to 0.2 units of heparin/ml of plasma.

11. The method of claim 8, wherein the amount of heparin administered results in a concentration of about 0.05 to 0.1 units of heparin/ml of plasma.

12. A method of inhibiting P-selectin mediated binding in a subject by administering an amount of heparin that does not produce substantial anticoagulant activity or undesirable bleeding.

13. The method of claim 12, wherein the amount of heparin administered results in a concentration of about 0.005 to 0.05 units of heparin/ml of plasma.

14. The method of claim 12, wherein the amount of heparin administered results in a concentration of about 0.005 to 0.02 units of heparin/ml of plasma.

15. A method of treating L-selectin and P-selectin related pathology by administering an amount of heparin that does not produce substantial anticoagulant activity or undesirable bleeding.

16. The method of claim 15, wherein the pathology is selected from the group consisting of ischemia, reperfusion injury, acute inflammation, chronic inflammation, and cancer metastasis.

17. A method of treating P-selectin related pathology by administering an amount of heparin that does not produce substantial anticoagulant activity or undesirable bleeding.

18. The method of claim 17, wherein the pathology is selected from the group consisting of ischemia, reperfusion injury, acute inflammation, chronic inflammation, and cancer metastasis.

19. The method of claim 1, wherein said administration is by injection.

20. The method of claim 19, wherein said injection is selected from the group consisting of intravenous and subcutaneous injection.

21. The method of claim 8, wherein said administration is by injection.

22. The method of claim 21, wherein said injection is selected from the group consisting of intravenous and subcutaneous injection.

23. The method of claim 15, wherein said administration is by injection.

24. The method of claim 23, wherein said injection is selected from the group consisting of intravenous and subcutaneous injection.

25. The method of claim 17, wherein said administration is by injection.

26. The method of claim 25, wherein said injection is selected from the group consisting of intravenous and subcutaneous injection.

* * * * *

UNITED STATES PATENT AND TRADEMARK OFFICE
CERTIFICATE OF CORRECTION

PATENT NO.    : 6,596,705 B1
DATED         : July 22, 2003
INVENTOR(S)   : Ajit Varki et al.

It is certified that error appears in the above-identified patent and that said Letters Patent is hereby corrected as shown below:

<u>Title page,</u>
Item [54], should read -- INHIBITION OF L-SELECTIN AND P-SELECTIN MEDIATED BINDING USING HEPARIN --

Signed and Sealed this

Third Day of February, 2004

JON W. DUDAS
*Acting Director of the United States Patent and Trademark Office*